US008247452B2

(12) United States Patent
DeFossa et al.

(10) Patent No.: US 8,247,452 B2
(45) Date of Patent: Aug. 21, 2012

(54) UREA- AND URETHANE-SUBSTITUTED ACYLUREAS, PROCESS FOR THEIR PREPARATION AND THEIR USE

(75) Inventors: Elisabeth DeFossa, Frankfurt (DE); Dieter Kadereit, Kelkheim (DE); Thomas Klabunde, Frankfurt (DE); Hans-Joerg Burger, Morristown, NJ (US); Andreas Herling, Bad Camberg (DE); Karl-Ulrich Wendt, Frankfurt (DE); Erich Von Roedern, Hattersheim (DE); Karl Schoenafinger, Alzenau (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 88 days.

(21) Appl. No.: 11/845,242

(22) Filed: Aug. 27, 2007

(65) Prior Publication Data

US 2008/0033042 A1 Feb. 7, 2008

Related U.S. Application Data

(62) Division of application No. 10/616,959, filed on Jul. 11, 2003, now Pat. No. 7,262,220.

(60) Provisional application No. 60/425,600, filed on Nov. 12, 2002.

(30) Foreign Application Priority Data

Jul. 11, 2002 (DE) ................................ 102 31 371

(51) Int. Cl.
*C07C 275/24* (2006.01)
*A61K 31/277* (2006.01)
(52) U.S. Cl. ............................. 514/585; 564/26; 564/48
(58) Field of Classification Search ........................ None
See application file for complete search history.

(56) References Cited

U.S. PATENT DOCUMENTS

| | | | |
|---|---|---|---|
| 4,665,235 A | 5/1987 | Brouwer et al. | |
| 4,783,485 A * | 11/1988 | Brouwer et al. | ............ 514/535 |
| 5,190,923 A | 3/1993 | Vincent et al. | |
| 6,221,633 B1 | 4/2001 | Ertl | |
| 6,221,897 B1 | 4/2001 | Frick et al. | |
| 6,245,744 B1 | 6/2001 | Frick et al. | |
| 6,342,512 B1 | 1/2002 | Kirsch | |
| 6,441,022 B1 | 8/2002 | Frick et al. | |
| 6,506,778 B2 | 1/2003 | Defossa | |
| 6,552,048 B2 | 4/2003 | Kirsch | |
| 6,566,340 B2 | 5/2003 | Frick et al. | |
| 6,569,835 B2 | 5/2003 | Frick et al. | |
| 6,624,185 B2 | 9/2003 | Glombik | |
| 6,642,269 B2 | 11/2003 | Frick et al. | |
| 6,812,250 B2 | 11/2004 | Defossa | |
| 6,884,812 B2 | 4/2005 | Glombik | |
| 6,897,198 B2 | 5/2005 | Frick et al. | |
| 7,019,023 B2 | 3/2006 | Frick et al. | |
| 7,138,414 B2 * | 11/2006 | Schoenafinger et al. | ...... 514/317 |
| 7,262,220 B2 * | 8/2007 | Defossa et al. | ............... 514/585 |
| 7,399,777 B2 | 7/2008 | Glombik | |

FOREIGN PATENT DOCUMENTS

| | | |
|---|---|---|
| EP | 0116729 | 8/1984 |
| EP | 0167197 | 1/1986 |
| EP | 0221847 | 5/1987 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/63208 | 10/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/85695 | 11/2001 |
| WO | WO 01/91752 | 12/2001 |

OTHER PUBLICATIONS

U.S. Appl. No. 09/662,649, filed Sep. 14, 2000.
U.S. Appl. No. 09/724,496, filed Nov. 28, 2000.
U.S. Appl. No. 10/978,674, filed Nov. 1, 2004, Defossa.
U.S. Appl. No. 09/703,883, filed Nov. 1, 2000.
Asakawa, A., et al., Cocaine-Amphetamine-Regulated Transcript Influences Energy Metabolism, Anxiety and Gastric Emptying in Mice, Hormone and Metabolic Research, 2001, vol. 33(9), pp. 554-558.

(Continued)

*Primary Examiner* — Yevegeny Valenrod
(74) *Attorney, Agent, or Firm* — Barbara E. Kurys; Scully, Scott, Murphy & Presser, P.C.

(57) ABSTRACT

The invention relates to urea- and urethane-substituted acylureas and to their physiologically tolerated salts and physiologically functional derivatives. In particular, the invention relates to the compounds of the formula I

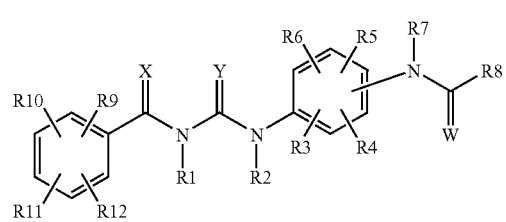

wherein the radicals have meanings described herein, and to their physiologically tolerated salts and to processes for their preparation. The compounds are suitable for example as antidiabetics.

3 Claims, No Drawings

OTHER PUBLICATIONS

Drueckes P et al., Photometric Microtiter Assay of Inorganic Phosphate in the Presence of Acid-Labile Organic Phosphates, Anal. Biochem, 1995, vol. 230(1), pp. 173-177.

Engers. H.D., et. al. et al., Kinetic Mechanism of Phosphorylase a. I. Initial Velocity Studies, Journal of Biochemistry, (1970), vol. 48, pp. 746-754.

Lee Daniel W., et al., Leptin Agonists as a Potential Approach to the Treatment of Obesity, Drugs of the Future, (2001), vol. 26, No. 9, pp. 873-881.

Okada Hiroshi et al., Synthesis and Antitumor Activities of Prodrugs of Benzoylphenylureas, Chem, Pharm. Bull., 1994, vol. 42(1), pp. 57-61.

Salvador Javier, et al., Perspectives in the Therapeutic Use of Leptin, Expert Opin. Pharmacother. (2001), vol. 2(10), pp. 1615-1622.

Tyle Praveen, Iontophoretic Devices for Drug Delivery, Pharmaceutical Research, 1986, vol. 3, No. 6, 318-326.

Zunft, H. et al., Carob Pulp Preparation for Treatment of Hypercholesterolemia, Advances in Therapy, 2001, vol. 18(5), pp. 230-236.

\* cited by examiner

UREA- AND URETHANE-SUBSTITUTED ACYLUREAS, PROCESS FOR THEIR PREPARATION AND THEIR USE

CROSS-REFERENCE TO RELATED APPLICATIONS

This application claims priority under 35 U.S.C. §119 to DE 10231371.7-42 filed Jul. 11, 2002. This application also claims priority under 35 U.S.C. §120 to U.S. Provisional No. 60/425,600, filed Nov. 12, 2002. Both of these documents are incorporated herein by reference in their entirety.

BACKGROUND OF THE INVENTION

1. Field of the Invention

The invention relates to urea- and urethane-substituted acylureas and to their physiologically tolerated salts and physiologically functional derivatives.

2. Description of the Prior Art

EP 0 221 847 describes compounds of similar structure for controlling pests.

SUMMARY OF THE INVENTION

In a preferred embodiment, the invention provides compounds which prevent and treat type 2 diabetes. The compounds of the invention produce a marked reduction in blood glucose levels.

In another preferred embodiment, the invention provides a pharmaceutical composition comprising one or more compounds of the instant invention and at least one other active ingredient.

In another preferred embodiment, the invention provides a pharmaceutical composition comprising one or more of the compounds of the instant invention.

In another preferred embodiment, the invention provides a method for reducing blood glucose, comprising administering to a subject in need thereof, one or more compounds of the instant invention.

In another preferred embodiment, the invention provides a method for treating type 2 diabetes, comprising administering to a subject in need thereof, one or more compounds of the instant invention.

In another preferred embodiment, the invention provides a method for treating disturbances of lipid and carbohydrate metabolism, comprising administering to a subject in need thereof, one or more compounds of the instant invention.

In another preferred embodiment, the invention provides a method for treating arteriosclerotic manifestations, comprising administering to a subject in need thereof, one or more compounds of the instant invention.

In another preferred embodiment, the invention provides a method for treating insulin resistance, comprising administering to a subject in need thereof, one or more compounds of the instant invention.

In another preferred embodiment, the invention provides a process for producing a pharmaceutical composition comprising one or more of the compounds of the invention, which comprises mixing the active ingredient with a pharmaceutically suitable carrier and converting this mixture into a form suitable for administration.

DETAILED DESCRIPTION OF THE PREFERRED EMBODIMENTS

The invention therefore relates to compounds of the formula I

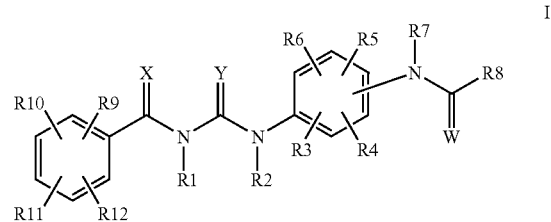

in which
W, X, Y are, independently of one another, O or S;
R9, R10, R11, R12 are, independently of one another, H, F, Cl, Br, OH, $CF_3$, $NO_2$, CN, $OCF_3$, O—$(C_1$-$C_6)$-alkyl, O—$(C_2$-$C_6)$-alkenyl, O—$(C_2$-$C_6)$-alkynyl, O—$SO_2$—$(C_1$-$C_4)$-alkyl, O—$SO_2$-phenyl, where the phenyl ring may be substituted up to twice by F, Cl, Br, CN, OR13, R13, $CF_3$, $OCF_3$, COOR13 or CON(R14)(R15), S—$(C_2$-$C_6)$-alkyl, S—$(C_2$-$C_6)$-alkenyl, S—$(C_2$-$C_6)$-alkynyl, SO—$(C_1$-$C_6)$-alkyl, $SO_2$—$(C_1$-$C_6)$-alkyl, $SO_2$—$NH_2$, $(C_1$-$C_6)$-alkyl, $(C_2$-$C_6)$-alkenyl, $(C_2$-$C_6)$-alkynyl, $(C_3$-$C_7)$-cycloalkyl, $(C_3$-$C_7)$-cycloalkyl-$(C_1$-$C_4)$-alkyl, —COOR13, $(C_1$-$C_6)$-alkylene-COOR13, CON(R14)(R15), —N(R14)(R15), $(C_1$-$C_6)$-alkylene-N(R14)(R15), NH—COR13, NH—CO-phenyl, NH—$SO_2$-phenyl or phenyl, where the phenyl ring may be substituted up to twice by F, Cl, Br, CN, OR13, R13, $CF_3$, $OCF_3$, COOR13 or CON(R14)(R15);
R13 is H, $(C_1$-$C_6)$-alkyl, $(C_2$-$C_6)$-alkenyl, $(C_2$-$C_6)$-alkynyl, $(C_3$-$C_7)$-cycloalkyl or $(C_3$-$C_7)$-cycloalkyl-$(C_1$-$C_4)$-alkyl;
R1, R2 are, independently of one another, H, $(C_1$-$C_6)$-alkyl, where alkyl may be substituted by OH, O—$(C_1$-$C_4)$-alkyl or N(R14)(R15), or O—$(C_1$-$C_6)$-alkyl, O—$(C_2$-$C_6)$-alkenyl, O—$(C_2$-$C_6)$-alkynyl, CO—$(C_1$-$C_6)$-alkyl, CO—$(C_2$-$C_6)$-alkenyl, CO—$(C_2$-$C_6)$-alkynyl, COOR13 or —COOR13, $(C_1$-$C_6)$-alkylene-COOR13;
R3, R4, R5, R6 are, independently of one another, H, F, Cl, Br, OH, $CF_3$, $NO_2$, CN, $OCF_3$, $(C_1$-$C_6)$-alkyl, $(C_2$-$C_6)$-alkenyl, $(C_2$-$C_6)$-alkynyl, O—$(C_1$-$C_{10})$-alkyl, O—$(C_2$-$C_{10})$-alkenyl, O—$(C_2$-$C_{10})$-alkynyl, S—$(C_1$-$C_5)$-alkyl, S—$(C_2$-$C_6)$-alkenyl, S—$(C_2$-$C_6)$-alkynyl, $(C_3$-$C_7)$-cycloalkyl, $(C_3$-$C_7)$-cycloalkyl-$(C_1$-$C_4)$-alkyl, where alkyl, alkenyl, alkynyl and cycloalkyl may be substituted more than once by F, Cl, Br, SO-phenyl, $SO_2$-phenyl, where the phenyl ring may be substituted by F, Cl, Br or R13, or OR13, COOR13, CON(R14)(R15), N(R14)(R15) or CO-heteroalkyl, O—SO—$(C_1$-$C_6)$-alkyl, O—$SO_2$—$(C_1$-$C_6)$-alkyl, O—$SO_2$—$(C_6$-$C_{10})$-aryl, O—$(C_6$-$C_{10})$-aryl, where aryl may be substituted up to twice by F, Cl, CN, OR13, R13, $CF_3$ or $OCF_3$, SO—$(C_1$-$C_6)$-alkyl, $SO_2$—$(C_1$-$C_6)$-alkyl, $SO_2$—$(C_6$-$C_{10})$-aryl, where the phenyl ring may be substituted up to twice by F, Cl, Br, CN, OR13, R13, $CF_3$, $OCF_3$, COOR13 or CON(R14)(R15), $SO_2$—N(R14)(R15), COOR13, CO-heteroalkyl, N(R14)(R15) or heteroalkyl;
R14, R15 are, independently of one another, H, $(C_1$-$C_6)$-alkyl, where alkyl may be substituted by N(R13)$_2$, $(C_2$-$C_6)$-alkenyl, $(C_2$-$C_6)$-alkynyl, $(C_3$-$C_7)$-cycloalkyl, $(C_3$-

$C_7$)-cycloalkyl-($C_1$-$C_4$)-alkyl, CO—($C_1$-$C_6$)-alkyl, COO—($C_1$-$C_6$)-alkyl, COO—($C_1$-$C_6$)-alkylene-OCO—($C_1$-$C_6$)-alkyl, CO-phenyl, COO-phenyl, COO—($C_1$-$C_6$)-alkenyl-phenyl, OH, O—($C_1$-$C_6$)-alkyl, O—($C_1$-$C_6$)-alkenyl-phenyl or $NH_2$;

or the radicals R14 and R15 form with the nitrogen atom to which they are bonded a 3-7-membered, saturated heterocyclic ring which may comprise up to 3 heteroatoms selected from N, O or S, where the heterocyclic ring may be substituted up to three times by F, Cl, Br, OH, oxo, N(R16)(R17) or ($C_1$-$C_4$)-alkyl;

R16, R17 are, independently of one another, H, ($C_1$-$C_6$)-alkyl, where alkyl may be substituted by N(R13)$_2$, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkyl, CO—($C_1$-$C_6$)-alkyl, COO—($C_1$-$C_6$)-alkyl, COO—($C_1$-$C_6$)-alkylene-OCO—($C_1$-$C_6$)-alkyl, CO-phenyl, COO-phenyl, COO—($C_1$-$C_6$)-alkenyl-phenyl, OH, O—($C_1$-$C_6$)-alkyl, O—($C_1$-$C_6$)-alkenyl-phenyl or $NH_2$;

heteroalkyl is a 3-7-membered, saturated or up to triunsaturated heterocyclic ring which may comprise up to 4 heteroatoms which correspond to N, O or S, where the heterocyclic ring may be substituted up to three times by F, Cl, Br, CN, oxo, ($C_1$-$C_4$)-alkyl, —COOR13, ($C_1$-$C_4$)-alkylene-COOR13, CON(R14)(R15), OR13, N(R14)(R15) or phenyl, where phenyl may be substituted by COOR13;

R7 is H, ($C_1$-$C_6$)-alkyl, where alkyl may be substituted by OR13 or N(R14)(R15), O—($C_1$-$C_6$)-alkyl, CO—($C_1$-$C_6$)-alkyl, —COOR13, or ($C_1$-$C_6$)-alkylene-COOR13;

R8 is N(R18)(R19) or OR20;

or R8 and R4 together form the group —NH—CO—;

R18, R19 are, independently of one another, H, ($C_1$-$C_{10}$)-alkyl, ($C_2$-$C_{10}$)-alkenyl, ($C_2$-$C_{10}$)-alkynyl, ($C_3$-$C_7$)-cycloalkyl, ($C_3$-$C_7$)-cycloalkyl-($C_1$-$C_6$)-alkyl, ($C_6$-$C_{10}$)-aryl, ($C_6$-$C_{10}$)-aryl-($C_1$-$C_4$)-alkyl, ($C_6$-$C_{10}$)-aryl-($C_2$-$C_4$)-alkenyl, ($C_6$-$C_{10}$)-aryl-($C_2$-$C_4$)-alkynyl, heteroaryl, heteroaryl-($C_1$-$C_4$)-alkyl, heteroaryl-($C_2$-$C_4$)-alkenyl, heteroaryl-($C_2$-$C_4$)-alkynyl, where alkyl, alkenyl, alkynyl and cycloalkyl may be substituted one or more times by F, Cl, CN, OR13, R13, $CF_3$, $OCF_3$, ($C_6$-$C_{10}$)-aryl, NH—C(=NR14)-N(R14)(R15), N(R14)(R15), C(=NR14)-N(R14)(R15), COOR13 or CON(R14)(R15), and where aryl may be substituted more than once by F, Cl, CN, O—($C_1$-$C_6$)-alkyl, O—($C_2$-$C_6$)-alkenyl, ($C_1$-$C_6$)-alkyl, ($C_2$-$C_6$)-alkenyl, CO—($C_1$-$C_6$)-alkyl, CO—($C_2$-$C_6$)-alkenyl, where alkyl and alkenyl may be substituted more than once by F, Cl, $CH_3$, $OCH_3$ or CN, NH—C(=NR14)-N(R14)(R15), N(R14)(R15), C(=NR14)-N(R14)(R15), COOR13, CON(R14)(R15), O-phenyl, phenyl or pyridyl; COOR13, CON—(R14)(R15), CO-heteroalkyl, CO—($C_6$-$C_{10}$)-aryl or $SO_2$—($C_6$-$C_{10}$)-aryl, where aryl may be substituted up to twice by F, Cl, CN, OH, ($C_1$-$C_6$)-alkyl, O—($C_1$-$C_6$)-alkyl, $CF_3$, $OCF_3$, COOR13 or CON(R14)(R15);

or the radicals R18 and R19 form with the nitrogen atom to which they are bonded a 3-7-membered, saturated heterocyclic ring which may comprise up to 3 heteroatoms selected from the group of N, O or S, where the heterocyclic ring may be substituted up to three times by F, Cl, Br, OH, oxo, N(R16)(R17) or ($C_1$-$C_4$)-alkyl;

R20 is ($C_1$-$C_{10}$)-alkyl, ($C_2$-$C_{10}$)-alkenyl, ($C_2$-$C_{10}$)-alkynyl, ($C_3$-$C_7$)-cycloalkyl, ($C_3$-$C_7$)-cycloalkyl-($C_1$-$C_6$)-alkyl, ($C_6$-$C_{10}$)-aryl, ($C_6$-$C_{10}$)-aryl-($C_1$-$C_4$)-alkyl, ($C_6$-$C_{10}$)-aryl-($C_2$-$C_4$)-alkenyl or ($C_6$-$C_{10}$)-aryl-($C_2$-$C_4$)-alkynyl, where aryl may be substituted more than once by F, Cl, CN, O—($C_1$-$C_6$)-alkyl, O—($C_2$-$C_6$)-alkenyl, ($C_1$-$C_6$)-alkyl, ($C_2$-$C_6$)-alkenyl, CO—($C_1$-$C_6$)-alkyl, CO—($C_2$-$C_6$)-alkenyl, where alkyl and alkenyl may be substituted more than once by F, Cl, $CH_3$, $OCH_3$ or CN, NH—C(=NR14)-N(R14)(R15), N(R14)(R15), C(=NR14)-N(R14)(R15), COOR13, CON(R14)(R15), O-phenyl, phenyl or pyridyl, where phenyl may be substituted by F, Cl, CN or ($C_1$-$C_6$)-alkyl;

and their physiologically tolerated salts, provided the radicals R6, R7, X, Y and R8 do not have the following meanings at the same time:
R6 is H, CL, $CF_3$, $CH_3$;
R7 is H;
X is O;
Y is O, S;
R8 is substituted or unsubstituted NH-phenyl.

In a preferred embodiment, the invention provides compounds of the formula 1a:

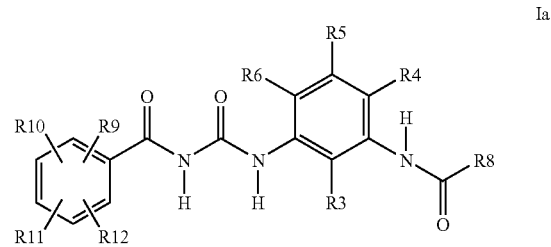

Ia wherein
R9 is F, Cl, Br, OH, $CF_3$, $NO_2$, CN, $OCF_3$, O—($C_1$-$C_6$)-alkyl, O—($C_2$-$C_6$)-alkenyl, O—($C_2$-$C_6$)-alkynyl, O—$SO_2$—($C_1$-$C_4$)-alkyl, O—$SO_2$-phenyl, where the phenyl ring may be substituted up to twice by F, Cl, Br, CN, OR13, R13, $CF_3$, $OCF_3$, COOR13 or CON(R14)(R15), or S—($C_1$-$C_6$)-alkyl, S—($C_2$-$C_6$)-alkenyl, S—($C_2$-$C_6$)-alkynyl, SO—($C_1$-$C_6$)-alkyl, $SO_2$—($C_1$-$C_6$)-alkyl, $SO_2$—$NH_2$, ($C_1$-$C_6$)-alkyl, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkyl, —COOR13, ($C_1$-$C_6$)-alkylene-COOR13, CON(R14)(R15), —N(R14)(R15), ($C_1$-$C_6$)-alkylene-N(R14)(R15), NH—COR13, NH—CO-phenyl, NH—$SO_2$-phenyl or phenyl, where the phenyl ring may be substituted up to twice by F, Cl, Br, CN, OR13, R13, $CF_3$, $OCF_3$, COOR13 or CON(R14)(R15);

R10, R11, R12 independently of one another are H, F, Cl, Br, OH, $CF_3$, $NO_2$, CN, $OCF_3$, O—($C_1$-$C_6$)-alkyl, O—($C_2$-$C_6$)-alkenyl, O—($C_2$-$C_6$)-alkynyl, O—$SO_2$—($C_1$-$C_4$)-alkyl, O—$SO_2$-phenyl, where the phenyl ring may be substituted up to twice by F, Cl, Br, CN, OR13, R13, $CF_3$, $OCF_3$, COOR13 or CON(R14)(R15), S—($C_1$-$C_6$)-alkyl, S—($C_2$-$C_6$)-alkenyl, S—($C_2$-$C_6$)-alkynyl, SO—($C_1$-$C_6$)-alkyl, $SO_2$—($C_1$-$C_6$)-alkyl, $SO_2$—$NH_2$, ($C_1$-$C_6$)-alkyl, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkyl, —COOR13, ($C_1$-$C_6$)-alkylene-COOR13, COOR13, CON(R14)(R15), —N(R14)(R15), ($C_1$-$C_6$)-alkylene-N(R14)(R15), $C_1$-$C_6$)-alkylene-N(R14)(R15), N(R14)(R15), NH—COR13, NH—CO-phenyl, NH—$SO_2$-phenyl or phenyl, where the phenyl ring may be substituted up to twice by F, Cl, Br, CN, OR13, R13, $CF_3$, $OCF_3$, COOR13 or CON(R14)(R15);

R13 is H, ($C_1$-$C_6$)-alkyl, ($C_2$-$C_6$)-alkenyl, ($C_2$-$C_6$)-alkynyl, ($C_3$-$C_7$)-cycloalkyl or ($C_3$-$C_7$)-cycloalkyl-($C_1$-$C_4$)-alkyl;

R3, R4, R5 are independently of one another H, F, Cl, Br, OH, $CF_3$, $NO_2$, CN, $OCF_3$, $(C_1-C_6)$-alkyl, $(C_2-C_6)$-alkenyl, $(C_2-C_6)$-alkynyl, O—$(C_1-C_{10})$-alkyl, O—$(C_2-C_{10})$-alkenyl, O—$(C_2-C_{10})$-alkynyl, S—$(C_1-C_6)$-alkyl, S—$(C_2-C_6)$-alkenyl, S—$(C_2-C_6)$-alkynyl, $(C_3-C_7)$-cycloalkyl, $(C_3-C_7)$-cycloalkyl-$(C_1-C_4)$-alkyl, where alkyl, alkenyl, alkynyl and cycloalkyl may be substituted more than once by F, Cl, Br, SO-phenyl, $SO_2$-phenyl, where the phenyl ring may be substituted by F, Cl, Br or R13, or OR13, COOR13, CON(R14)(R15), N(R14)(R15) or CO-heteroalkyl, O—SO—$(C_1-C_6)$-alkyl, O—$SO_2$—$(C_1-C_6)$-alkyl, O—$SO_2$—$(C_6-C_{10})$-aryl, O—$(C_6-C_{10})$-aryl, where aryl may be substituted up to twice by F, Cl, CN, OR13, R13, $CF_3$ or $OCF_3$, SO—$(C_1-C_6)$-alkyl, $SO_2$—$(C_1-C_6)$-alkyl, $SO_2$—$(C_6-C_{10})$-aryl, where the phenyl ring may be substituted up to twice by F, Cl, Br, CN, OR13, R13, $CF_3$, $OCF_3$, COOR13 or CON(R14)(R15), $SO_2$—N(R14)(R15), COOR13, CO-heteroalkyl, N(R14)(R15) or heteroalkyl;

R6 is F, Cl, Br, OH, $CF_3$, $NO_2$, CN, $OCF_3$, $(C_1-C_6)$-alkyl, $(C_2-C_6)$-alkenyl, $(C_2-C_6)$-alkynyl, O—$(C_1-C_{10})$-alkyl, O—$(C_2-C_{10})$-alkenyl, O—$(C_2-C_{10})$-alkynyl, S—$(C_1-C_6)$-alkyl, S—$(C_2-C_6)$-alkenyl, S—$(C_2-C_6)$-alkynyl, $(C_3-C_7)$-cycloalkyl, $(C_3-C_7)$-cycloalkyl-$(C_1-C_4)$-alkyl, where alkyl, alkenyl, alkynyl and cycloalkyl may be substituted more than once by F, Cl, Br, SO-phenyl, $SO_2$-phenyl, where the phenyl ring may be substituted by F, Cl, Br or R13, or OR13, COOR13, CON(R14)(R15), N(R14)(R15) or CO-heteroalkyl, or O—SO—$(C_1-C_6)$-alkyl, O—$SO_2$—$(C_1-C_6)$-alkyl, O—$SO_2$—$(C_6-C_{10})$-aryl, O—$(C_6-C_{10})$-aryl, where aryl may be substituted up to twice by F, Cl, CN, OR13, R13, $CF_3$ or $OCF_3$, or SO—$(C_1-C_6)$-alkyl, $SO_2$—$(C_1-C_6)$-alkyl, $SO_2$—$(C_6-C_{10})$-aryl, where the phenyl ring may be substituted up to twice by F, Cl, Br, CN, OR13, R13, $CF_3$, $OCF_3$, COOR13 or CON(R14)(R15), or $SO_2$—N(R14)(R15), COOR13, CO-heteroalkyl, N(R14)(R15) or heteroalkyl;

R14, R15 independently of one another are H, $(C_1-C_6)$-alkyl, where alkyl may be substituted by $N(R13)_2$, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkyl, CO—$(C_1-C_6)$-alkyl, COO—$(C_1-C_6)$-alkyl, COO—$(C_1-C_6)$-alkylene-OCO—$(C_1-C_6)$-alkyl, CO-phenyl, COO-phenyl, COO—$(C_1-C_6)$-alkenyl-phenyl, OH, O—$(C_1-C_6)$-alkyl, O—$(C_1-C_6)$-alkenyl-phenyl or $NH_2$;

or the radicals R14 and R15 form with the nitrogen atom to which they are bonded a 3-7-membered, saturated heterocyclic ring which may comprise up to 3 heteroatoms selected from the group of N, O or S, where the heterocyclic ring may be substituted up to three times by F, Cl, Br, OH, oxo, N(R16)(R17) or $(C_1-C_4)$-alkyl;

R16, R17 independently of one another are H, $(C_1-C_6)$-alkyl, where alkyl may be substituted by $N(R13)_2$, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkyl, CO—$(C_1-C_6)$-alkyl, COO—$(C_1-C_8)$-alkyl, COO—$(C_1-C_6)$-alkylene-OCO—$(C_1-C_6)$-alkyl, CO-phenyl, COO-phenyl, COO—$(C_1-C_6)$-alkenyl-phenyl, OH, O—$(C_1-C_6)$-alkyl, O—$(C_1-C_6)$-alkenyl-phenyl or $NH_2$;

heteroalkyl is a 3-7-membered, saturated or up to triunsaturated heterocyclic ring which may comprise up to 4 heteroatoms selected from N, O or S, where the heterocyclic ring may be substituted up to three times by F, Cl, Br, CN, oxo, $(C_1-C_4)$-alkyl, —COOR13, $(C_1-C_4)$-alkylene-COOR13, COOR13, CON(R14)(R15), OR13 or N(R14)(R15) or phenyl, where phenyl may be substituted by COOR13;

R8 is N(R18)(R19) or OR20;

or R8 and R4 together form the group —NH—CO—;

R18, R19 independently of one another are H, $(C_1-C_{10})$-alkyl, $(C_2-C_{10})$-alkenyl, $(C_2-C_{10})$-alkynyl, $(C_3-C_7)$-cycloalkyl, $(C_3-C_7)$-cycloalkyl-$(C_1-C_6)$-alkyl, $(C_6-C_{10})$-aryl, $(C_6-C_{10})$-aryl-$(C_1-C_4)$-alkyl, $(C_6-C_{10})$-aryl-$(C_2-C_4)$-alkenyl, $(C_6-C_{10})$-aryl-$(C_2-C_4)$-alkynyl, heteroaryl, heteroaryl-$(C_1-C_4)$-alkyl, heteroaryl-$(C_2-C_4)$-alkenyl, heteroaryl-$(C_2-C_4)$-alkynyl, where alkyl, alkenyl, alkynyl and cycloalkyl may be substituted more than once by F, Cl, CN, OR13, R13, $CF_3$, $OCF_3$, $(C_6-C_{10})$-aryl, NH—C(=NR14)-N(R14)(R15), N(R14)(R15), C(=NR14)-N(R14)(R15), COOR13 or CON(R14)(R15), and where aryl may be substituted more than once by F, Cl, CN, O—$(C_1-C_6)$-alkyl, O—$(C_2-C_6)$-alkenyl, $(C_1-C_6)$-alkyl, $(C_2-C_6)$-alkenyl, CO—$(C_1-C_6)$-alkyl, CO—$(C_2-C_6)$-alkenyl, where alkyl and alkenyl may be substituted more than once by F, Cl, $CH_3$, $OCH_3$ or CN, or NH—C(=NR14)-N(R14)(R15), N(R14)(R15), C(=NR14)-N(R14)(R15), COOR13, CON(R14)(R15), O-phenyl, phenyl or pyridyl; COOR13, CON—(R14)(R15), CO-heteroalkyl, CO—$(C_6-C_{10})$-aryl or $SO_2$—$(C_6-C_{10})$-aryl, where aryl may be substituted up to twice by F, Cl, CN, OH, $(C_1-C_6)$-alkyl, O—$(C_1-C_6)$-alkyl, $CF_3$, $OCF_3$, COOR13 or CON(R14)(R15);

or the radicals R18 and R19 form together with the nitrogen atom to which they are bonded a 3-7-membered, saturated heterocyclic ring which may comprise up to 3 heteroatoms selected from the group of N, O or S, where the heterocyclic ring may be substituted up to three times by F, Cl, Br, OH, oxo, N(R16)(R17) or $(C_1-C_4)$-alkyl;

R20 is $(C_1-C_{10})$-alkyl, $(C_2-C_{10})$-alkenyl, $(C_2-C_{10})$-alkynyl, $(C_3-C_7)$-cycloalkyl, $(C_3-C_7)$-cycloalkyl-$(C_1-C_6)$-alkyl, $(C_6-C_{10})$-aryl, $(C_6-C_{10})$-aryl-$(C_1-C_4)$-alkyl, $(C_6-C_{10})$-aryl-$(C_2-C_4)$-alkenyl or $(C_6-C_{10})$-aryl-$(C_2-C_4)$-alkynyl, where aryl may be substituted more than once by F, Cl, CN, O—$(C_1-C_6)$-alkyl, O—$(C_2-C_6)$-alkenyl, $(C_1-C_6)$-alkyl, $(C_2-C_6)$-alkenyl, CO—$(C_1-C_6)$-alkyl, CO—$(C_2-C_6)$-alkenyl, where alkyl and alkenyl may be substituted more than once by F, Cl, $CH_3$, $OCH_3$ or CN, or NH—C(=NR14)-N(R14)(R15), N(R14)(R15), C(=NR14)-N(R14)(R15), COOR13, CON(R14)(R15), O-phenyl, phenyl or pyridyl, where phenyl may be substituted by F, Cl, CN or $(C_1-C_6)$-alkyl;

and their physiologically tolerated salts, provided the radical R8 is not phenyl.

Preferably, compounds of formula 1a have the following meanings:

R9, R10, R11 independently of one another are F or Cl;

R12 is H;

R13 is H, $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkyl;

R6 is F, Cl, $CF_3$, $OCF_3$, $(C_1-C_6)$-alkyl, $(C_2-C_6)$-alkenyl, $(C_2-C_6)$-alkynyl, O—$(C_1-C_{10})$-alkyl, O—$(C_2-C_{10})$-alkenyl, O—$(C_2-C_{10})$-alkynyl, $(C_3-C_7)$-cycloalkyl, $(C_3-C_7)$-cycloalkyl-$(C_1-C_4)$-alkyl, N(R14)(R15) or Cl; heteroalkyl, where alkyl, alkenyl, alkynyl and cycloalkyl may be substituted more than once by F, COOR13, CON(R14)(R15) or $N(R_{14})(R_{15})$;

R14, R15 are independently of one another H, $(C_1-C_6)$-alkyl, where alkyl may be substituted by $N(R13)_2$;

Heteroalkyl is a 3-7-membered, saturated or up to triunsaturated heterocyclic ring which may comprise up to 4 heteroatoms which correspond to N, O or S, where the heterocyclic ring may be substituted up to three times by F, Cl, Br, CN, oxo, $(C_1-C_4)$-alkyl, —COOR13, $(C_1-C_4)$-alkylene-COOR13, CON(R14)(R15), OR13 or N(R14)(R15) or phenyl, where phenyl may be substituted by COOR13;

R8 is N(R18)(R19) or OR20;

or R8 and R4 together form the group —NH—CO—;

R18, R19 are independently of one another H, $(C_1-C_{10})$-alkyl, $(C_2-C_{10})$-alkenyl, $(C_2-C_{10})$-alkynyl, $(C_3-C_7)$-cycloalkyl, $(C_3-C_7)$-cycloalkyl-$(C_1-C_6)$-alkyl, $(C_6-C_{10})$-aryl, $(C_6-C_{10})$-aryl-$(C_1-C_4)$-alkyl, $(C_6-C_{10})$-aryl-$(C_2-C_4)$-alkenyl, $(C_6-C_{10})$-aryl-$(C_2-C_4)$-alkynyl, heteroaryl, heteroaryl-$(C_1-C_4)$-alkyl, heteroaryl-$(C_2-C_4)$-alkenyl, heteroaryl-$(C_2-C_4)$-alkynyl, where alkyl, alkenyl, alkynyl and cycloalkyl may be substituted more than once by F, Cl, CN, OR13, R13, $CF_3$, $OCF_3$, $(C_6-C_{10})$-aryl, NH—C(=NR14)-N(R14)(R15), N(R14)(R15), C(=NR14)-N(R14)(R15), COOR13 or CON(R14)(R15), and where aryl may be substituted more than once by F, Cl, CN, O—$(C_1-C_6)$-alkyl, O—$(C_2-C_6)$-alkenyl, $(C_1-C_6)$-alkyl, $(C_2-C_6)$-alkenyl, CO—$(C_1-C_6)$-alkyl, CO—$(C_2-C_6)$-alkenyl, where alkyl and alkenyl may be substituted more than once by F, Cl, $CH_3$, $OCH_3$ or CN, or NH—C(=NR14)-N(R14)(R15), N(R14)(R15), C(=NR14)-N(R14)(R15), COOR13, CON(R14)(R15), O-phenyl, phenyl or pyridyl; COOR13, CON—(R14)(R15), CO-heteroalkyl, CO—$(C_6-C_{10})$-aryl or $SO_2$—$(C_6-C_{10})$-aryl, where aryl may be substituted up to twice by F, Cl, CN, OH, $(C_1-C_6)$-alkyl, O—$(C_1-C_6)$-alkyl, $CF_3$, $OCF_3$, COOR13 or CON(R14)(R15);

or the radicals R18 and R19 form together with the nitrogen atom to which they are bonded a 3-7-membered, saturated heterocyclic ring which may comprise up to 2 further heteroatoms from the group of N, O or S, where the heterocyclic ring may be substituted up to three times by F, Cl, Br, OH, oxo, N(R16)(R17) or $(C_1-C_4)$-alkyl;

R20 is $(C_1-C_{10})$-alkyl, $(C_2-C_{10})$-alkenyl, $(C_2-C_{10})$-alkynyl, $(C_3-C_7)$-cycloalkyl, $(C_3-C_7)$-cycloalkyl-$(C_1-C_6)$-alkyl, $(C_6-C_{10})$-aryl, $(C_6-C_{10})$-aryl-$(C_1-C_4)$-alkyl, $(C_6-C_{10})$-aryl-$(C_2-C_4)$-alkenyl or $(C_6-C_{10})$-aryl-$(C_2-C_4)$-alkynyl, where aryl may be substituted more than once by F, Cl, CN, or O—$(C_1-C_6)$-alkyl.

The alkyl radicals in the substituents R1, R2, R3, R4, R5, R6, R7, R8, R9, R10, R11, R12, R13, R14, R15, R16, R17, R18, R19 or R20 may be both straight-chain and branched.

If radicals or substituents may occur more than once in the compounds of the formula I, such as, for example, COOR13, they may all, independently of one another, have the stated meanings and be identical or different.

The invention relates to compounds of the formula I in the form of their racemates, racemic mixtures and pure enantiomers, and to their diastereomers and mixtures thereof.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

The compound(s) of formula (I) may also be administered in combination with another active ingredient.

In another preferred embodiment, the invention provides a pharmaceutical composition comprising one or more of the compounds of the instant invention and at least one other active ingredient. The other active ingredient may comprise one or more antidiabetics, hypoglycemic active ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists (bromocriptine, Doprexin), lipase/amylase inhibitors, PPAR modulators, RXR modulators or TR-β agonists or amphetamines.

In another preferred embodiment, the invention provides a process for producing a pharmaceutical composition comprising one or more of the compounds of the invention, which comprises mixing the active ingredient with a pharmaceutically suitable carrier and converting this mixture into a form suitable for administration.

In another preferred embodiment, the invention provides a pharmaceutical composition comprising one or more of the compounds of the instant invention.

In another preferred embodiment, the invention provides a method for reducing blood glucose, comprising administering to a subject in need thereof, one or more compounds of the instant invention.

In another preferred embodiment, the invention provides a method for treating type 2 diabetes, comprising administering to a subject in need thereof, one or more compounds of the instant invention.

In another preferred embodiment, the invention provides a method for treating disturbances of lipid and carbohydrate metabolism, comprising administering to a subject in need thereof, one or more compounds of the instant invention.

In another preferred embodiment, the invention provides a method for treating arteriosclerotic manifestations, comprising administering to a subject in need thereof, one or more compounds of the instant invention.

In another preferred embodiment, the invention provides a method for treating insulin resistance, comprising administering to a subject in need thereof, one or more compounds of the instant invention.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, wafers, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine. The instant invention covers other dosage forms used in the art, for example, those with micronized or nanosized ingredients.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are: all antidiabetics mentioned in the Rote Liste 2001, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantuse® (see www.lantus.com), fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US00/11833, PCT/US00/11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with a bile acid absorption inhibitor (see, for example, U.S. Pat. Nos. 6,245,744 or 6,221,897).

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512).

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipicide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipicide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., in: Hormone and Metabolic Research (2001), 33(9), 554-558), NPY antagonists, e.g. naphthalene- 1-sulfonic acid {4-[(4-aminoquinazolin-2-ylamino)methyl]cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), decoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention. The following compounds are exemplary pharmaceutical substances that may be used in combination with the instant compounds.

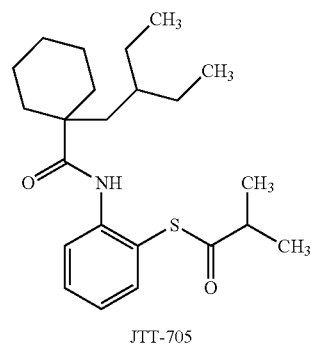

JTT-705

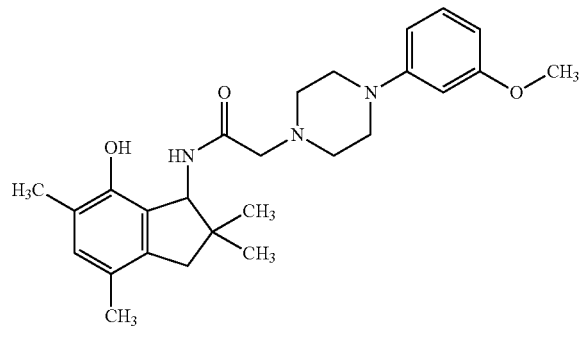

OPC-14117

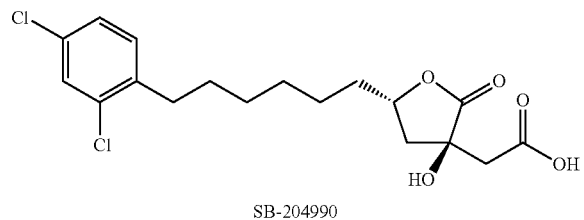

SB-204990

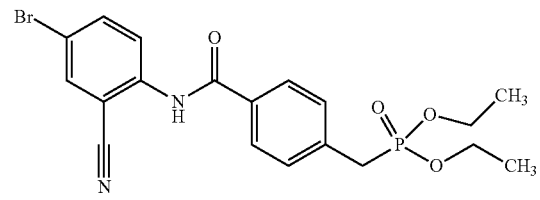

NO-1886

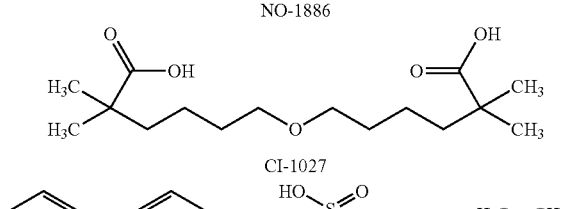

CI-1027

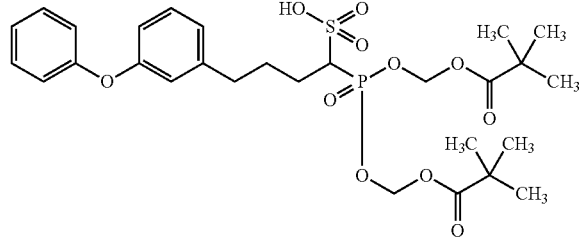

BMS-188494

-continued

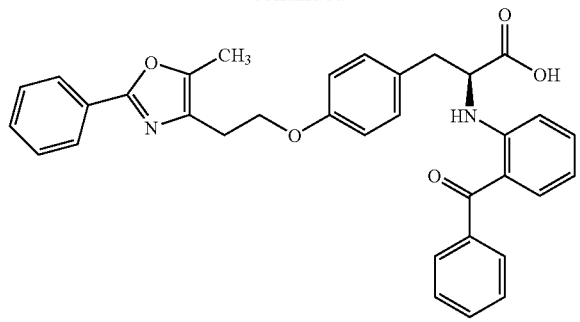

GI 262570

-continued

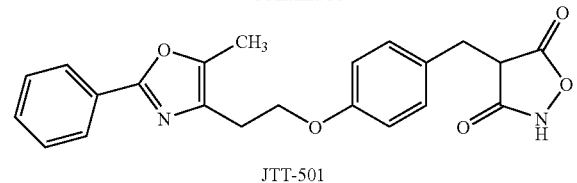

JTT-501

The examples detailed below serve to illustrate the invention, but without restricting it.

TABLE 1

Examples of the formula I

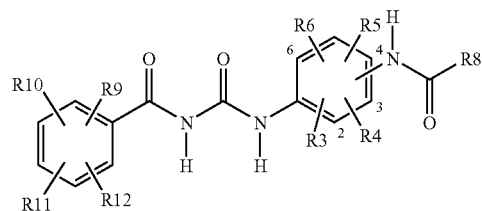

| Ex. | R9, R10, R11, R12 | R3 | R4 | R5 | R6 | Linkage | R8 | MS* |
|---|---|---|---|---|---|---|---|---|
| 1 | 2-Cl-4,5-F$_2$ | 2-H | 4-H | 5-H | 6-OCH$_3$ | 3 | NHCH$_3$ | ok |
| 2 | 2-Cl-4,5-F$_2$ | 2-H | 4-COOC$_2$H$_5$ | 5-H | 6-OCH$_3$ | 3 | NHCH$_3$ | ok |
| 3 | 2-Cl-4-F | 2-H | 3-COOH | 4-H | 5-H | 6 | OCH$_3$ | ok |
| 4 | 2-Cl-4,5-F$_2$ | 2-H | 4-H | 5-H | 6-OCF$_3$ | 3 | NHC$_2$H$_5$ | ok |
| 5 | 2-Cl-4,5-F$_2$ | 2-H | 4-H | 5-H | ![methyl crotonate at 6] | 3 | NHC$_2$H$_5$ | ok |
| 6 | 2-Cl-4,5-F$_2$ | 2-H | 4-H | 5-H | ![crotonic acid at 6] | 3 | NHC$_2$H$_5$ | ok |
| 7 | 2-Cl-4,5-F$_2$ | 2-H | 4-H | 5-H | 6-N(CH$_3$)$_2$ | 3 | NHC$_2$H$_5$ | ok |
| 8 | 2-Cl-4,5-F$_2$ | 2-H | 4-H | 5-H | ![N-methylpyrrolidine at 6] | 3 | NHC$_2$H$_5$ | ok |
| 9 | 2-Cl-4,5-F$_2$ | 2-H | 4-H | 5-H | 6-Cl | 3 | NHC$_2$H$_5$ | ok |
| 10 | 2-Cl-4,5-F$_2$ | 2-H | 4-H | 5-H | 6-OCH$_3$ | 3 | NHC$_2$H$_5$ | ok |
| 11 | 2-Cl-4,5-F$_2$ | 2-H | 4-COOC$_2$H$_5$ | 5-H | 6-OCH$_3$ | 3 | NHC$_2$H$_5$ | ok |
| 12 | 2-Cl-4,5-F$_2$ | 2-H | 4-H | 5-H | 6-OCH$_3$ | 3 | ![NH-methyl-2-CF$_3$-phenyl] | ok |
| 13 | 2-Cl-4,5-F$_2$ | 2-H | 4-H | 5-H | 6-OCH$_3$ | 3 | ![NH-methyl-4-COOC$_2$H$_5$-phenyl] | ok |

TABLE 1-continued
Examples of the formula I
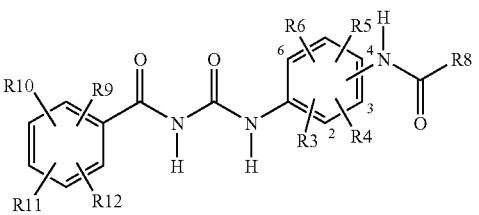
| Ex. | R9, R10, R11, R12 | R3 | R4 | R5 | R6 | Linkage | R8 | MS* |
|---|---|---|---|---|---|---|---|---|
| 14 | 2-Cl-4,5-F$_2$ | 2-H | 4-H | 5-H | 6-OCH$_3$ | 3 | 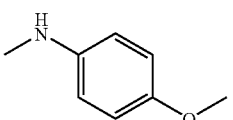 | ok |
| 15 | 2-Cl-4,5-F$_2$ | 2-H | 4-H | 5-H | 6-OCH$_3$ | 3 | 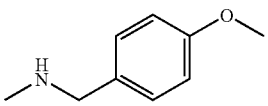 | ok |
| 16 | 2-Cl-4,5-F$_2$ | 2-H | 4-H | 5-H | 6-OCH$_3$ | 3 | 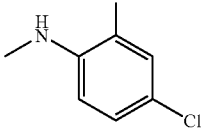 | ok |
| 17 | 2-Cl-4,5-F$_2$ | 2-H | 4-H | 5-H | 6-OCH$_3$ | 3 |  | ok |
| 18 | 2-Cl-4,5-F$_2$ | 2-H | 4-H | 5-H | 6-OCH$_3$ | 3 | NHCH$_2$COOC$_2$H$_5$ | ok |
| 19 | 2-Cl-4,5-F$_2$ | 2-H | 4-H | 5-H | 6-OCH$_3$ | 3 | 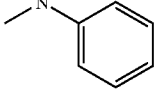 | ok |
| 20 | 2-Cl-4,5-F$_2$ | 2-H | 4-H | 5-H | 6-OCH$_3$ | 3 | 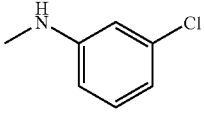 | ok |
| 21 | 2-Cl-4,5-F$_2$ | 2-H | 4-H | 5-H | 6-OCH$_3$ | 3 | 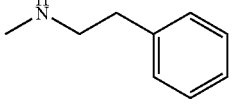 | ok |
| 22 | 2-Cl-4,5-F$_2$ | 2-H | 4-H | 5-H | 6-OCH$_3$ | 3 | 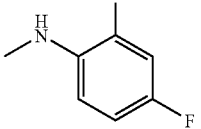 | ok |
| 23 | 2-Cl-4,5-F$_2$ | 2-H | 4-H | 5-H | 6-OCH$_3$ | 3 | 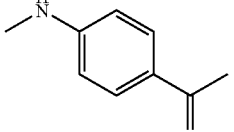 | ok |

TABLE 1-continued
Examples of the formula I
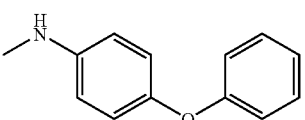
| Ex. | R9, R10, R11, R12 | R3 | R4 | R5 | R6 | Linkage | R8 | MS* |
|---|---|---|---|---|---|---|---|---|
| 24 | 2-Cl-4,5-F$_2$ | 2-H | 4-H | 5-H | 6-OCH$_3$ | 3 | 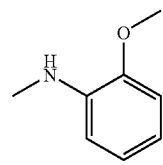 | ok |
| 25 | 2-Cl-4,5-F$_2$ | 2-H | 4-H | 5-H | 6-OCH$_3$ | 3 | 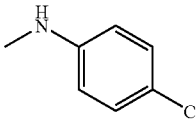 | ok |
| 26 | 2-Cl-4,5-F$_2$ | 2-H | 4-H | 5-H | 6-OCH$_3$ | 3 | 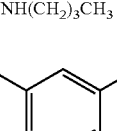 | ok |
| 27 | 2-Cl-4,5-F$_2$ | 2-H | 4-H | 5-H | 6-OCH$_3$ | 3 | NH(CH$_2$)$_3$CH$_3$ | ok |
| 28 | 2-Cl-4,5-F$_2$ | 2-H | 4-H | 5-H | 6-OCH$_3$ | 3 | 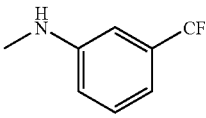 | ok |
| 29 | 2-Cl-4,5-F$_2$ | 2-H | 4-H | 5-H | 6-OCH$_3$ | 3 | 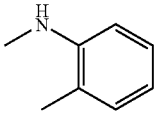 | ok |
| 30 | 2-Cl-4,5-F$_2$ | 2-H | 4-H | 5-H | 6-OCH$_3$ | 3 | NHCH(CH$_3$)$_2$ | ok |
| 31 | 2-Cl-4,5-F$_2$ | 2-H | 4-H | 5-H | 6-OCH$_3$ | 3 | NH(CH$_2$)$_5$CH$_3$ | ok |
| 32 | 2-Cl-4,5-F$_2$ | 2-H | 4-H | 5-H | 6-OCH$_3$ | 3 | 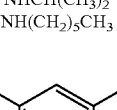 | ok |
| 33 | 2-Cl-4,5-F$_2$ | 2-H | 4-H | 5-H | 6-OCH$_3$ | 3 | 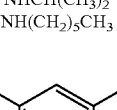 | ok |
| 34 | 2-Cl-4,5-F$_2$ | 2-H | 4-H | 5-H | 6-OCH$_3$ | 3 | 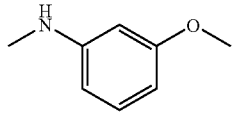 | ok |
| 35 | 2-Cl-4,5-F$_2$ | 2-H | 4-H | 5-H | 6-OCH$_3$ | 3 | NH(CH$_2$)$_2$CH$_3$ | ok |

TABLE 1-continued

Examples of the formula I

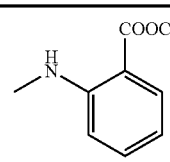

| Ex. | R9, R10, R11, R12 | R3 | R4 | R5 | R6 | Linkage | R8 | MS* |
|---|---|---|---|---|---|---|---|---|
| 36 | 2-Cl-4,5-F$_2$ | 2-H | 4-H | 5-H | 6-OCH$_3$ | 3 | 2-(NHCH$_3$)-C$_6$H$_4$-COOCH$_3$ | ok |
| 37 | 2-Cl-4,5-F$_2$ | 2-H | 4-H | 5-H | 6-OCH$_3$ | 3 | 3-(NHCH$_3$)-C$_6$H$_4$-COOC$_2$H$_5$ | ok |
| 38 | 2-Cl-4,5-F$_2$ | 2-H | 4-H | 5-H | 6-OCH$_3$ | 3 | 3-(NHCH$_3$)-C$_6$H$_4$-COCH$_3$ | ok |
| 39 | 2-Cl-4,5-F$_2$ | 2-H | 4-H | 5-H | 6-OCH$_3$ | 3 | 4-(NHCH$_3$)-C$_6$H$_4$-CN | ok |
| 40 | 2-Cl-4,5-F$_2$ | 2-H | 4-H | 5-H | 6-OCH$_3$ | 3 | 3-(NHCH$_3$)-C$_6$H$_4$-COOCH$_3$ | ok |
| 41 | 2-Cl-4,5-F$_2$ | 2-H | 4-H | 5-H | 6-OCH$_3$ | 3 | 2-(NHCH$_3$)-biphenyl | ok |
| 42 | 2-Cl-4,5-F$_2$ | 2-H | 4-H | 5-H | 6-OCH$_3$ | 3 | 3,4-F$_2$-C$_6$H$_3$-NHCH$_3$ | ok |
| 43 | 2-Cl-4,5-F$_2$ | 2-H | 4-H | 5-H | 6-OCH$_3$ | 3 | NH(CH$_2$)$_4$CH$_3$ | ok |
| 44 | 2-Cl-4,5-F$_2$ | 2-H | 4-H | 5-H | 6-OCH$_3$ | 3 | 4-(OCF$_3$)-C$_6$H$_3$-NHCH$_3$ | ok |

TABLE 1-continued
Examples of the formula I
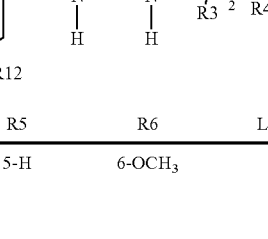
| Ex. | R9, R10, R11, R12 | R3 | R4 | R5 | R6 | Linkage | R8 | MS* |
|---|---|---|---|---|---|---|---|---|
| 45 | 2-Cl-4,5-F$_2$ | 2-H | 4-H | 5-H | 6-OCH$_3$ | 3 | 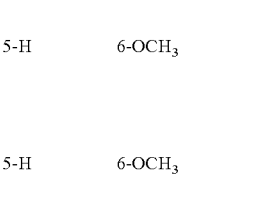 | ok |
| 46 | 2-Cl-4,5-F$_2$ | 2-H | 4-H | 5-H | 6-OCH$_3$ | 3 | 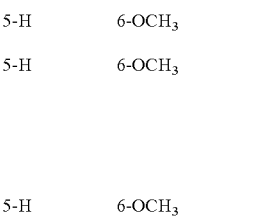 | ok |
| 47 | 2-Cl-4,5-F$_2$ | 2-H | 4-H | 5-H | 6-OCH$_3$ | 3 | 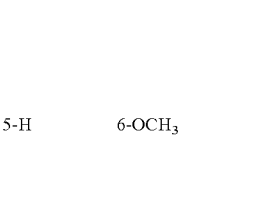 | ok |
| 48 | 2-Cl-4,5-F$_2$ | 2-H | 4-H | 5-H | 6-OCH$_3$ | 3 | NH(CH$_2$)$_2$COOC$_2$H$_5$ | ok |
| 49 | 2-Cl-4,5-F$_2$ | 2-H | 4-H | 5-H | 6-OCH$_3$ | 3 | 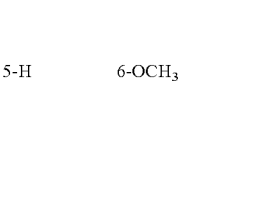 | ok |
| 50 | 2-Cl-4,5-F$_2$ | 2-H | 4-H | 5-H | 6-OCH$_3$ | 3 | 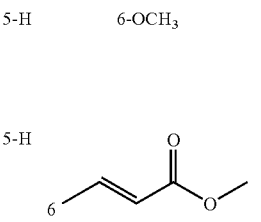 | ok |
| 51 | 2-Cl-4,5-F$_2$ | 2-H | 4-H | 5-H | 6-OCH$_3$ | 3 | 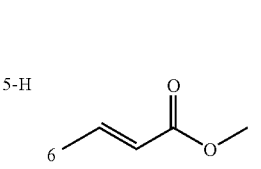 | ok |
| 52 | 2-Cl-4,5-F$_2$ | 2-H | 4-H | 5-H | 6-OCH$_3$ | 3 |  | ok |
| 53 | 2-Cl-4,5-F$_2$ | 2-H | 4-H | 5-H | 6-OCH$_3$ | 3 | | ok |
| 54 | 2-Cl-4,5-F$_2$ | 2-H | 4-H | 5-H | | 3 | | ok |
| 55 | 2-Cl-4,5-F$_2$ | 2-H | 4-H | 5-H | | 3 | | ok |

TABLE 1-continued

Examples of the formula I

| Ex. | R9, R10, R11, R12 | R3 | R4 | R5 | R6 | Linkage | R8 | MS* |
|---|---|---|---|---|---|---|---|---|
| 56 | 2-Cl-4,5-F$_2$ | 2-H | 4-H | 5-H | 6-(E)-CH=CH-C(O)OCH$_3$ | 3 | NH-(4-methoxyphenyl) | ok |
| 57 | 2-Cl-4,5-F$_2$ | 2-H | 4-H | 5-H | 6-(E)-CH=CH-C(O)OCH$_3$ | 3 | NH-CH$_2$-(4-methoxyphenyl) | ok |
| 58 | 2-Cl-4,5-F$_2$ | 2-H | 4-H | 5-H | 6-(E)-CH=CH-C(O)OCH$_3$ | 3 | NH-(4-OCHF$_2$-phenyl) | ok |
| 59 | 2-Cl-4,5-F$_2$ | 2-H | 4-H | 5-H | 6-(E)-CH=CH-C(O)OCH$_3$ | 3 | NHCH$_2$COOC$_2$H$_5$ | ok |
| 60 | 2-Cl-4,5-F$_2$ | 2-H | 4-H | 5-H | 6-(E)-CH=CH-C(O)OCH$_3$ | 3 | NH-phenyl | ok |
| 61 | 2-Cl-4,5-F$_2$ | 2-H | 4-H | 5-H | 6-(E)-CH=CH-C(O)OCH$_3$ | 3 | NH-CH$_2$CH$_2$-phenyl | ok |
| 62 | 2-Cl-4,5-F$_2$ | 2-H | 4-H | 5-H | 6-(E)-CH=CH-C(O)OCH$_3$ | 3 | NH-(2,4-difluorophenyl) | ok |
| 63 | 2-Cl-4,5-F$_2$ | 2-H | 4-H | 5-H | 6-(E)-CH=CH-C(O)OCH$_3$ | 3 | NH-(2-fluorophenyl) | ok |
| 64 | 2-Cl-4,5-F$_2$ | 2-H | 4-H | 5-H | 6-(E)-CH=CH-C(O)OCH$_3$ | 3 | NH-(4-acetylphenyl) | ok |

TABLE 1-continued

Examples of the formula I

| Ex. | R9, R10, R11, R12 | R3 | R4 | R5 | R6 | Linkage | R8 | MS* |
|---|---|---|---|---|---|---|---|---|
| 65 | 2-Cl-4,5-F₂ | 2-H | 4-H | 5-H | methyl (E)-but-2-enoate (6-position) | 3 | N-methyl-4-phenoxyaniline | ok |
| 66 | 2-Cl-4,5-F₂ | 2-H | 4-H | 5-H | methyl (E)-but-2-enoate (6-position) | 3 | N-methyl-2-methoxyaniline | ok |
| 67 | 2-Cl-4,5-F₂ | 2-H | 4-H | 5-H | methyl (E)-but-2-enoate (6-position) | 3 | N-methyl-4-chloroaniline | ok |
| 68 | 2-Cl-4,5-F₂ | 2-H | 4-H | 5-H | methyl (E)-but-2-enoate (6-position) | 3 | NH(CH₂)₃CH₃ | ok |
| 69 | 2-Cl-4,5-F₂ | 2-H | 4-H | 5-H | methyl (E)-but-2-enoate (6-position) | 3 | N-methyl-3-(trifluoromethyl)aniline | ok |
| 70 | 2-Cl-4,5-F₂ | 2-H | 4-H | 5-H | methyl (E)-but-2-enoate (6-position) | 3 | N-methyl-2-methylaniline | ok |
| 71 | 2-Cl-4,5-F₂ | 2-H | 4-H | 5-H | methyl (E)-but-2-enoate (6-position) | 3 | NHCH(CH₃)₂ | ok |
| 72 | 2-Cl-4,5-F₂ | 2-H | 4-H | 5-H | methyl (E)-but-2-enoate (6-position) | 3 | NH(CH₂)₅CH₃ | ok |
| 73 | 2-Cl-4,5-F₂ | 2-H | 4-H | 5-H | methyl (E)-but-2-enoate (6-position) | 3 | N-methyl-3-methylaniline | ok |
| 74 | 2-Cl-4,5-F₂ | 2-H | 4-H | 5-H | methyl (E)-but-2-enoate (6-position) | 3 | N-methyl-4-fluoroaniline | ok |

TABLE 1-continued

Examples of the formula I

| Ex. | R9, R10, R11, R12 | R3 | R4 | R5 | R6 | Linkage | R8 | MS* |
|---|---|---|---|---|---|---|---|---|
| 75 | 2-Cl-4,5-F$_2$ | 2-H | 4-H | 5-H | 6-CH=CH-COOCH$_3$ | 3 | NH(CH$_2$)$_2$CH$_3$ | ok |
| 76 | 2-Cl-4,5-F$_2$ | 2-H | 4-H | 5-H | 6-CH=CH-COOCH$_3$ | 3 | 2-(COOCH$_3$)-C$_6$H$_4$-NH- | ok |
| 77 | 2-Cl-4,5-F$_2$ | 2-H | 4-H | 5-H | 6-CH=CH-COOCH$_3$ | 3 | 3-(COOC$_2$H$_5$)-C$_6$H$_4$-NH- | ok |
| 78 | 2-Cl-4,5-F$_2$ | 2-H | 4-H | 5-H | 6-CH=CH-COOCH$_3$ | 3 | 3-(COCH$_3$)-C$_6$H$_4$-NH- | ok |
| 79 | 2-Cl-4,5-F$_2$ | 2-H | 4-H | 5-H | 6-CH=CH-COOCH$_3$ | 3 | 3-(COOCH$_3$)-C$_6$H$_4$-NH- | ok |
| 80 | 2-Cl-4,5-F$_2$ | 2-H | 4-H | 5-H | 6-CH=CH-COOCH$_3$ | 3 | 2-biphenyl-NH- | ok |
| 81 | 2-Cl-4,5-F$_2$ | 2-H | 4-H | 5-H | 6-CH=CH-COOCH$_3$ | 3 | 3,4-F$_2$-C$_6$H$_3$-NH- | ok |
| 82 | 2-Cl-4,5-F$_2$ | 2-H | 4-H | 5-H | 6-CH=CH-COOCH$_3$ | 3 | 2-(OCF$_3$)-C$_6$H$_4$-NH- | ok |

TABLE 1-continued

Examples of the formula I

| Ex. | R9, R10, R11, R12 | R3 | R4 | R5 | R6 | Linkage | R8 | MS* |
|---|---|---|---|---|---|---|---|---|
| 83 | 2-Cl-4,5-F$_2$ | 2-H | 4-H | 5-H | 6-(E)-CH=CH-C(O)OCH$_3$ | 3 | NH(CH$_2$)$_4$CH$_3$ | ok |
| 84 | 2-Cl-4,5-F$_2$ | 2-H | 4-H | 5-H | 6-(E)-CH=CH-C(O)OCH$_3$ | 3 | NH-(4-OCF$_3$-C$_6$H$_4$) | ok |
| 85 | 2-Cl-4,5-F$_2$ | 2-H | 4-H | 5-H | 6-(E)-CH=CH-C(O)OCH$_3$ | 3 | NH-CH$_2$-(4-F-C$_6$H$_4$) | ok |
| 86 | 2-Cl-4,5-F$_2$ | 2-H | 4-H | 5-H | 6-(E)-CH=CH-C(O)OCH$_3$ | 3 | NH-CH$_2$-C$_6$H$_5$ | ok |
| 87 | 2-Cl-4,5-F$_2$ | 2-H | 4-H | 5-H | 6-(E)-CH=CH-C(O)OCH$_3$ | 3 | NH-CH$_2$-CH=CH$_2$ | ok |
| 88 | 2-Cl-4,5-F$_2$ | 2-H | 4-H | 5-H | 6-(E)-CH=CH-C(O)OCH$_3$ | 3 | NH(CH$_2$)$_2$COOC$_2$H$_5$ | ok |
| 89 | 2-Cl-4,5-F$_2$ | 2-H | 4-H | 5-H | 6-(E)-CH=CH-C(O)OCH$_3$ | 3 | NH-(3-F-C$_6$H$_4$) | ok |
| 90 | 2-Cl-4,5-F$_2$ | 2-H | 4-H | 5-H | 6-(E)-CH=CH-C(O)OCH$_3$ | 3 | NH-cyclohexyl | ok |
| 91 | 2-Cl-4,5-F$_2$ | 2-H | 4-H | 5-H | 6-(E)-CH=CH-C(O)OCH$_3$ | 3 | NH-(3-pyridyl) | ok |
| 92 | 2-Cl-4,5-F$_2$ | 2-H | 4-H | 5-H | 6-(E)-CH=CH-C(O)OCH$_3$ | 3 | NH-(2-OC$_6$H$_5$-C$_6$H$_4$) | ok |

TABLE 1-continued

Examples of the formula I

| Ex. | R9, R10, R11, R12 | R3 | R4 | R5 | R6 | Linkage | R8 | MS* |
|---|---|---|---|---|---|---|---|---|
| 93 | 2-Cl-4,5-F$_2$ | 2-H | 4-H | 5-H | 6-(E)-CH=CHC(O)OCH$_3$ | 3 | NHCH$_2$-(4-methylphenyl) | ok |
| 94 | 2-Cl-4,5-F$_2$ | 2-H | 4-H | 5-H | 6-OCHF$_2$ | 3 | OCH$_3$ | ok |
| 95 | 2-Cl-4,5-F$_2$ | 2-H | 4-H | 5-H | 6-OCHF$_2$ | 3 | NHC$_2$H$_5$ | ok |
| 96 | 2-Cl-4,5-F$_2$ | 2-H | 4-H | 5-H | 6-OCH$_3$ | 3 | O(CH$_2$)$_2$CH$_3$ | ok |
| 97 | 2-Cl-4,5-F$_2$ | 2-H | 4-H | 5-H | 6-OCH$_3$ | 3 | OCH$_2$CH=CH$_2$ (allyloxy with methoxy) | ok |
| 98 | 2-Cl-4,5-F$_2$ | 2-H | 4-H | 5-H | 6-OCH$_3$ | 3 | O(CH$_2$)$_3$CH$_3$ | ok |
| 99 | 2-Cl-4,5-F$_2$ | 2-H | 4-H | 5-H | 6-OCH$_3$ | 3 | OCH$_2$CH(CH$_3$)$_2$ | ok |
| 100 | 2-Cl-4,5-F$_2$ | 2-H | 4-H | 5-H | 6-OCH$_3$ | 3 | OC$_2$H$_5$ | ok |
| 101 | 2-Cl-4,5-F$_2$ | 2-H | 4-H | 5-H | 6-OCH$_3$ | 3 | OCH$_2$C≡CCH$_3$ | ok |
| 102 | 2-Cl-4,5-F$_2$ | 2-H | 4-H | 5-H | 6-OCH$_3$ | 3 | O-(4-methylphenyl)-OCH$_3$ | ok |
| 103 | 2-Cl-4,5-F$_2$ | 2-H | 4-H | 5-H | 6-OCH$_3$ | 3 | O(CH$_2$)$_2$CH=CH$_2$ | ok |
| 104 | 2-Cl-4,5-F$_2$ | 2-H | 4-H | 5-H | 6-OCH$_3$ | 3 | O(CH$_2$)$_5$CH$_3$ | ok |
| 105 | 2-Cl-4,5-F$_2$ | 2-H | 4-H | 5-H | 6-(E)-CH=CHC(O)OCH$_3$ | 3 | O(CH$_2$)$_2$CH$_3$ | ok |
| 106 | 2-Cl-4,5-F$_2$ | 2-H | 4-H | 5-H | 6-(E)-CH=CHC(O)OCH$_3$ | 3 | OCH$_2$CH=CH$_2$ | ok |
| 107 | 2-Cl-4,5-F$_2$ | 2-H | 4-H | 5-H | 6-(E)-CH=CHC(O)OCH$_3$ | 3 | O(CH$_2$)$_3$CH$_3$ | ok |
| 108 | 2-Cl-4,5-F$_2$ | 2-H | 4-H | 5-H | 6-(E)-CH=CHC(O)OCH$_3$ | 3 | OCH$_2$CH(CH$_3$)$_2$ | ok |
| 109 | 2-Cl-4,5-F$_2$ | 2-H | 4-H | 5-H | 6-(E)-CH=CHC(O)OCH$_3$ | 3 | OC$_2$H$_5$ | ok |
| 110 | 2-Cl-4,5-F$_2$ | 2-H | 4-H | 5-H | 6-(E)-CH=CHC(O)OCH$_3$ | 3 | O-(4-chlorophenyl)-OCH$_3$ | ok |
| 111 | 2-Cl-4,5-F$_2$ | 2-H | 4-H | 5-H | 6-(E)-CH=CHC(O)OCH$_3$ | 3 | OCH$_2$C≡CCH$_3$ | ok |

TABLE 1-continued

Examples of the formula I

| Ex. | R9, R10, R11, R12 | R3 | R4 | R5 | R6 | Linkage | R8 | MS* |
|---|---|---|---|---|---|---|---|---|
| 112 | 2-Cl-4,5-F$_2$ | 2-H | 4-H | 5-H | 6-(E)-CH=CH-C(O)OCH$_3$ | 3 | 2-Cl-6-OCH$_3$-phenoxy | ok |
| 113 | 2-Cl-4,5-F$_2$ | 2-H | 4-H | 5-H | 6-(E)-CH=CH-C(O)OCH$_3$ | 3 | O(CH$_2$)$_2$CH=CH$_2$ | ok |
| 114 | 2-Cl-4,5-F$_2$ | 2-H | 4-H | 5-H | 6-(E)-CH=CH-C(O)OCH$_3$ | 3 | O(CH$_2$)$_5$CH$_3$ | ok |
| 115 | 2-Cl-4,5-F$_2$ | 2-H | 4-H | 5-H | 6-OC$_2$H$_5$ | 3 | OCH$_3$ | ok |
| 116 | 2-Cl-4,5-F$_2$ | 2-H | 4-H | 5-H | 6-OC$_2$H$_5$ | 3 | NHC$_2$H$_5$ | ok |
| 117 | 2-Cl-4,5-F$_2$ | 2-H | 4-H | 5-H | 6-O(CH$_2$)$_2$CH$_3$ | 3 | OCH$_3$ | ok |
| 118 | 2-Cl-4,5-F$_2$ | 2-H | 4-H | 5-H | 6-O(CH$_2$)$_2$CH$_3$ | 3 | NHC$_2$H$_5$ | ok |
| 119 | 2-Cl-4,5-F$_2$ | 2-H | 4-H | 5-H | 6-O(CH$_2$)$_3$CH$_3$ | 3 | OCH$_3$ | ok |
| 120 | 2-Cl-4,5-F$_2$ | 2-H | 4-H | 5-H | 6-O(CH$_2$)$_3$CH$_3$ | 3 | NHC$_2$H$_5$ | ok |
| 121 | 2-Cl-4,5-F$_2$ | 2-H | 4-H | 5-H | 6-N(CH$_3$)C$_2$H$_5$ × TFA | 3 | OCH$_3$ | ok |
| 122 | 2-Cl-4,5-F$_2$ | 2-H | 4-H | 5-H | 6-N(CH$_3$)C$_2$H$_5$ × TFA | 3 | NHC$_2$H$_5$ | ok |
| 123 | 2-Cl-4,5-F$_2$ | 2-H | 4-H | 5-H | 6-N(CH$_3$)CH$_2$CH$_2$N(CH$_3$)$_2$ × TFA | 3 | OCH$_3$ | ok |
| 124 | 2-Cl-4,5-F$_2$ | 2-H | 4-H | 5-H | 6-N(CH$_3$)CH$_2$CH$_2$N(CH$_3$)$_2$ × TFA | 3 | NHC$_2$H$_5$ | ok |
| 125 | 2,4-Cl$_2$ | 2-H | 4-H | 5-H | 6-H | 3 | NHCH$_3$ | ok |
| 126 | 2,4-Cl$_2$ | 2-H | 4-H | 5-H | 6-Cl | 3 | NHCH$_3$ | ok |
| 127 | 2,4-Cl$_2$ | 2-H | 4-H | 5-H | 6-OCH$_3$ | 3 | NHCH$_3$ | ok |
| 128 | 2,4-Cl$_2$ | 2-H | 4-H | 5-H | 6-OCH$_3$ | 3 | NH(CH$_2$)$_2$COOC$_2$H$_5$ | ok |
| 129 | 2-Cl-4,5-F$_2$ | 2-H | 4-H | 5-H | 6-Cl | 3 | NHCH$_3$ | ok |
| 130 | 2,4-Cl$_2$ | 2-H | 3-H | 5-H | 6-H | 4 | NHCH$_3$ | ok |
| 131 | 2,4-Cl$_2$ | 2-H | 3-H | 5-H | 6-H | 4 | NH(CH$_2$)$_3$NH$_2$ × TFA | ok |

TABLE 1-continued

Examples of the formula I

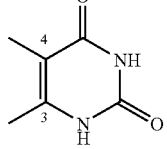

| Ex. | R9, R10, R11, R12 | R3 | R4 | R5 | R6 | Linkage | R8 | MS* |
|---|---|---|---|---|---|---|---|---|
| 132 | 2-Cl-4,5-F$_2$ | 2-H | — | 5-H | 6-OCH$_3$ | 3 | (4,5-dimethyl-2-oxo-2,3-dihydropyrimidin-1-yl carbonyl) | ok |

*The statement "MS is ok" means that a mass spectrum or HPLC/MS was recorded and the molecular peak (molecular mass + H$^+$) was detected therein.

The compounds of the formula I are distinguished by beneficial effects on glucose metabolism; in particular they lower the blood glucose level and are suitable for the treatment of type 2 diabetes. The compounds can therefore be employed alone or in combination with other blood glucose-lowering active ingredients (antidiabetics).

The compounds of the formula I are further suitable for the treatment of late complications of diabetes such as, for example, nephropathy, retinopathy, neuropathy and myocardial infarction, peripheral arterial occlusive diseases, thromboses, arteriosclerosis, syndrome X, obesity, inflammations, immune diseases, autoimmune diseases such as, for example, AIDS, asthma, osteoporosis, cancer, psoriasis, Alzheimer's, schizophrenia and infectious diseases.

The activity of the compounds was assayed as follows:
Glycogen Phosphorylase a Activity Assay The effect of compounds on the activity of the active form of glycogen phosphorylase (GPa) was measured in the reverse direction by following the synthesis of glycogen from glucose 1-phosphate by determining the liberation of inorganic phosphate. All the reactions were carried out as duplicate determinations in microtiter plates with 96 wells (Half Area Plates, Costar No 3696), measuring the change in absorption owing to the formation of the reaction product at the wavelength specified hereinafter in a Multiskan Ascent Elisa Reader (Lab Systems, Finland). In order to measure the GPa enzymic activity in the reverse direction, the general method of Engers et al. (Engers H D, Shechosky S, Madsen N B, Can J Biochem 1970 July; 48(7):746-754) was used to measure the conversion of glucose 1-phosphate into glycogen and inorganic phosphate, with the following modifications: human glycogen phosphorylase a (for example with 0.76 mg of protein/ml (Aventis Pharma Deutschland GmbH), dissolved in buffer solution E (25 mM β-glycerophosphate, pH 7.0, 1 mM EDTA and 1 mM dithiothreitol) was diluted with buffer T (50 mM hepes, pH 7.0, 100 mM KCl, 2.5 mM EDTA, 2.5 mM MgCl$_2$6H$_2$O) and addition of 5 mg/ml glycogen to a concentration of 10 µg of protein/ml. Test substances were prepared as 10 mM solution in DMSO and diluted to 50 µM with buffer solution T. To 10 µl of this solution were added 10 µl of 37.5 mM glucose, dissolved in buffer solution T, and 5 mg/ml glycogen, plus 10 µl of a solution of human glycogen phosphorylase a (10 µg of protein/ml) and 20 µl of glucose 1-phosphate, 2.5 mM. The baseline glycogen phosphorylase a activity in the absence of test substance was determined by adding 10 µl of buffer solution T (0.1% DMSO). The mixture was incubated at room temperature for 40 minutes, and the liberated organic phosphate was measured by the general method of Drueckes et al. (Drueckes P, Schinzel R, Palm D, Anal Biochem 1995 Sep. 1; 230(1):173-177) with the following modifications: 50 µl of a stop solution of 7.3 mM ammonium molybdate, 10.9 mM zinc acetate, 3.6% ascorbic acid, 0.9% SDS are added to 50 µl of the enzyme mixture. After incubation at 45° C. for 60 minutes, the absorption at 820 nm was measured. To determine the background absorption, in a separate mixture the stop solution was added immediately after addition of the glucose 1-phosphate solution. This test was carried out with a concentration of 10 µM of the test substance in order to determine the particular inhibition of glycogen phosphorylase a in vitro by the test substance.

TABLE 2

Biological activity

| Ex. | % inhibition at 10 µM |
|---|---|
| 2 | 96 |
| 3 | 53 |
| 4 | 89 |
| 7 | 100 |
| 13 | 103 |
| 14 | 70 |
| 21 | 75 |
| 26 | 61 |
| 42 | 55 |
| 44 | 40 |
| 65 | 60 |
| 76 | 73 |
| 90 | 89 |
| 91 | 99 |
| 92 | 78 |
| 104 | 66 |
| 108 | 52 |
| 110 | 73 |
| 113 | 83 |
| 114 | 48 |
| 121 | 99 |
| 125 | 74 |
| 127 | 102 |

TABLE 2-continued

Biological activity

| Ex. | % inhibition at 10 µM |
|---|---|
| 130 | 28 |
| 132 | 97 |

It is evident from the table that the compounds of the formula I inhibit the activity of glycogen phosphorylase a and thus are very suitable for lowering the blood glucose level. They are therefore particularly suitable for the prevention and treatment of type 2 diabetes.

The preparation of some examples is described in detail below, and the other compounds of the formula I were obtained analogously:

Experimental Part

The numbering of the following examples corresponds to the tables above.

Example 1

1-{3-[3-(2-Chloro-4,5-difluorobenzoyl)ureido]-4-methoxyphenyl}-3-methylurea a) 2-Chloro-4,5-difluorobenzoyl isocyanate 2-Chloro-4,5-difluorobenzamide was dissolved in dichloromethane, mixed with 1.5 eq. of oxalyl chloride and heated to reflux for 16 hours. The reaction mixture was concentrated under high vacuum and employed in stage b without further purification.

b) 1-(2-Chloro-4,5-difluorobenzoyl)-3-(2-methoxy-5-nitrophenyl)urea 4.0 g (23.8 mmol) of 2-methoxy-5-nitroaniline were dissolved in 10 ml of N-methyl-2-pyrrolidinone, and 5.2 g (23.8 mmol) of 2-chloro-4,5-difluorobenzoyl isocyanate were added. Slight warming occurred. After 15 minutes at room temperature, diethyl ether was added, and the resulting precipitate was filtered off with suction. 6.6 g (79%) of the desired product were obtained.

c) 1-(5-Amino-2-methoxyphenyl)-3-(2-chloro-4,5-difluorobenzoyl)urea 5.8 g (25.9 mmol) of tin dichloride hydrate were added to 2.0 g (5.2 mmol) of 1-(2-chloro-4,5-difluorobenzoyl)-3-(2-methoxy-5-nitrophenyl)urea in 20 ml of ethyl acetate/methanol mixture at 70° C. After 1 hour, 30 ml of N-methyl-2-pyrrolidinone were added, and the mixture was stirred for a further 2 hours. After cooling, the reaction mixture was made basic and the resulting precipitate was filtered off with suction. The phases were separated. The organic phase was then washed three times with water, dried and concentrated under high vacuum. 1.2 g (67%) of the desired product were obtained.

d) 1-{3-[3-(2-Chloro-4,5-difluorobenzoyl)ureido]-4-methoxyphenyl}-3-methylurea 600 mg (1.7 mmol) of 1-(5-amino-2-methoxyphenyl)-3-(2-chloro-4,5-difluoro-benzoyl)urea were dissolved in 5 ml of acetonitrile, and 69 mg (1.7 mmol) of methyl isocyanate were added. After stirring at room temperature for one hour, the resulting precipitate was filtered off with suction. 638 mg (91%) of the desired product were obtained.

Example 3

3-[3-(2-Chloro-4-fluorobenzoyl)ureido]-4-methoxycarbonylaminobenzoic acid a) 2-Chloro-4-fluorobenzoyl isocyanate 1.64 g (6 mmol) of 2-chloro-4-fluorobenzamide were dissolved in 3 ml of dichloromethane and, at 0° C. and under a nitrogen atmosphere, 0.8 ml (9.3 mmol) of oxalyl chloride was added, and the mixture was heated to reflux for 9 hours. The reaction mixture was concentrated under high vacuum and afforded 1.17 g (5.8 mmol) of the desired product, which was employed as solution in dichloromethane (1 mmol in 1.7 ml of solution) in stage b.

b) 4-Amino-3-[3-(2-chloro-4-fluorobenzoyl)ureido]benzoic acid 150 mg (1 mmol) of 3,4-diaminobenzoic acid were dissolved in 2 ml of N-methyl-2-pyrrolidinone and, at 0° C., 1 ml (1.2 mmol) of the 2-chloro-4-fluorobenzoyl isocyanate/dichloromethane solution prepared in stage a was added. The resulting precipitate was filtered off with suction. The crude mixture (500 mg) was purified by column chromatography (dichloromethane/methanol=98/2 to 93/7). 80 mg (25%) of the desired product were obtained.

c) 3-[3-(2-Chloro-4-fluorobenzoyl)ureido]-4-methoxycarbonylaminobenzoic acid SA-2919

28 mg (0.08 mmol) of 4-amino-3-[3-(2-chloro-4-fluorobenzoyl)ureido]benzoic acid were dissolved in 0.5 ml of N-methyl-2-pyrrolidinone and stirred with 0.02 ml (0.24 mmol) of pyridine and 0.007 ml of methyl chloroformate at room temperature for 4 hours. Water and acetic acid were added, and the resulting precipitate was filtered off with suction. 18 mg (55%) of the desired product were obtained.

Melting point: decomposition>400° C.

Example 54

Methyl 3-{2-[3-(2-chloro-4,5-difluorobenzoyl)ureido]-4-[3-(2-trifluoromethylphenyl)-ureido]phenyl}acrylate a) Methyl 3-{2-[3-(2-chloro-4,5-difluorobenzoyl)ureido]-4-nitrophenyl}acrylate F-33579-057

4.5 g (20.3 mmol) of methyl 3-(2-amino-4-nitrophenyl)acrylate were stirred with 4.41 g (20.3 mmol) of 2-chloro-4,5-difluorobenzoyl isocyanate (Example 1a) in 50 ml acetonitrile at 50° C. for one hour. The reaction mixture was then concentrated, the residue was stirred with diethyl ether, and the resulting solid was filtered off with suction. 8.5 g (95%) of the desired product were obtained.

b) Methyl 3-{4-amino-2-[3-(2-chloro-4,5-difluorobenzoyl)ureido]phenyl}acrylate 8.5 g (19.3 mmol) of methyl 3-{2-[3-(2-chloro-4,5-difluorobenzoyl)ureido]-4-nitro-phenyl}acrylate were suspended in 60 ml of a mixture of glacial acetic acid and concentrated hydrochloric acid (10:1) and heated to 70° C. Then 8.85 g (135.3 mmol) of zinc powder were added. After 30 minutes, the mixture was cooled, the solid was filtered off with suction, and the filtrate was concentrated. The residue was taken up in ethyl acetate and washed with a 10% strength sodium bicarbonate solution. The organic phase was dried and concentrated. 7.9 g (100%) of the desired product were obtained.

c) Methyl 3-{2-[3-(2-chloro-4,5-difluorobenzoyl)ureido]-4-[3-(2-trifluoromethyl-phenyl)ureido]phenyl}acrylate 100 mg (0.24 mmol) of methyl 3-{4-amino-2-[3-(2-chloro-4,5-difluorobenzoyl)-ureido]phenyl}acrylate were dissolved in 1 ml of acetonitrile and mixed with 2-trifluoromethylphenyl isocyanate and shaken at 60° C. for 14 hours. The resulting precipitate was filtered off with suction, and 16 mg (11%) of the desired product were obtained.

Example 110

Methyl (E)-3-[2-[3-(2-chloro-4,5-difluorobenzoyl)ureido]-4-(4-chloro-phenoxycarbonylamino)phenyl]acrylate 100 mg (0.24 mmol) of methyl 3-{4-amino-2-[3-(2-chloro-4,5-difluorobenzoyl)-ureido]phenyl}acrylate (example 54b) were reacted in 2 ml of dimethylformamide with potassium carbonate and 4-chlorophenyl chloroformate. The precipitate resulting after 4 hours was filtered off with suction. Preparative HPLC (column: Waters Xterra™MS $C_{18}$, 5 µm, 30×100 mm, mobile phases: A: $H_2O$+0.2% trifluoroacetic acid, B: acetonitrile, gradient: 2.5 minutes 90% A/10% B to 17.5 minutes 10% A/90% B) resulted in 12 mg (9%) of the desired product.

Example 132

1-(2-Chloro-4,5-difluorobenzoyl)-3-(6-methoxy-2,4-dioxo-1,2,3,4-tetrahydro-quinazolin-7-yl)urea a) N-(4-Methoxy-2-methylphenyl)acetamide 41.1 g (0.3 mol) of 4-methoxy-2-methylphenylamine and 37 g (0.5 mol) of dimethylethylamine were dissolved in 50 ml of tetrahydrofuran, and 35.7 g (0.35 mol) of acetic anhydride were added while stirring. The solution heated to boiling during this. It was stirred at room temperature for 1 hour and cooled to 0° C. The resulting precipitate was filtered off with suction and washed several times with a little cold tetrahydrofuran and dried. 40 g (75%) of colorless crystals of the desired product were obtained.

b) N-(4-Methoxy-2-methyl-5-nitrophenyl)acetamide 34 g (0.19 mol) of N-(4-methoxy-2-methylphenyl)acetamide were added in small portions to a mixture of 40 ml of glacial acetic acid and 70 ml of fuming nitric acid at −10 to −15° C. These portions were such that the temperature did not rise above −10° C. The reaction mixture was then poured onto ice. The resulting precipitate was filtered off with suction and washed with water, ethanol and diethyl ether. 22.5 g (53%) of the desired product were obtained.

c) 2-Acetylamino-5-methoxy-4-nitrobenzoic acid 11.2 g (50 mmol) of N-(4-methoxy-2-methyl-5-nitrophenyl)acetamide and 8.5 g (62.5 mmol) of anhydrous magnesium sulfate were suspended in 500 ml of water and heated to 85° C. Over the course of 30 minutes, a solution of 21.8 g (138 mmol) of potassium permanganate in 250 ml of water was added dropwise. The reaction mixture was stirred at 85° C. for 3 hours and then filtered hot to remove manganese dioxide. The latter was extracted by boiling three times with 100 ml of water each time. The combined aqueous phases were again filtered hot and concentrated to about 150 ml in vacuo. The residue was acidified to pH 1-2 with concentrated hydrochloric acid and cooled to 0° C. The resulting product was filtered off with suction, washed with water and diethyl ether, dried and reacted without further purification in the next stage.

d) 2-Amino-5-methoxy-4-nitrobenzoic acid 7.5 g of 2-acetylamino-5-methoxy-4-nitrobenzoic acid (crude mixture from stage c) were heated to reflux in 50 ml of water and 20 ml of concentrated hydrochloric acid for 3 hours. The reaction mixture was concentrated in vacuo and purified by column chromatography (silica gel, dichloromethane/isopropanol=9/1). 3.1 g (50%) of the desired product were obtained.

e) 6-Methoxy-7-nitro-1H-benzo[d][1,3]oxazine-2,4-dione 2.0 g (9.4 mmol) of 2-amino-5-methoxy-4-nitrobenzoic acid were dissolved in 20 ml of chloroform and 10 ml of tetrahydrofuran, and 20 ml of 20% strength phosgene solution (1.8 M in toluene) were added. After 3 hours under reflux, a further 10 ml of phosgene solution were added at 60° C., and the mixture was stirred at 60° C. for a further 12 hours. The phosgene was distilled off and the residue was concentrated in vacuo after addition of toluene several times. 2.2 g (100%) of the desired product were obtained.

f) 2-Amino-5-methoxy-4-nitrobenzamide 476 mg (2 mmol) of 6-methoxy-7-nitro-1H-benzo[d][1,3]oxazine-2,4-dione and 1.5 g (20 mmol) of ammonium acetate were dissolved in 20 ml of acetic acid and heated at 105° C. for 3 hours. The reaction mixture was then poured into ice-water and slowly brought to pH 7 with solid sodium bicarbonate. The aqueous phase was extracted with ethyl acetate. The organic phase was washed with water, dried and concentrated in vacuo. The crude product was triturated with diethyl ether, and the resulting precipitate was filtered off with suction. 285 mg (68%) of the desired product were obtained.

g) 6-Methoxy-7-nitro-1H-quinazoline-2,4-dione 108 mg (0.5 mmol) of 2-amino-5-methoxy-4-nitrobenzamide were dissolved in 5 ml of tetrahydrofuran and 5 ml of chloroform, and oxalyl chloride (solution in toluene) was added. The mixture was stirred at 60° C. for 5 hours and then concentrated in vacuo. Addition of toluene was followed by renewed concentration. 120 mg (100%) of the desired product were obtained.

h) 7-Amino-6-methoxy-1H-quinazoline-2,4-dione 120 mg (0.5 mmol) of 6-methoxy-7-nitro-1H-quinazoline-2,4-dione were taken up in a mixture of 5 ml of tetrahydrofuran, 5 ml of methanol and 5 ml of acetic acid and hydrogenated with palladium catalysis at room temperature for 3 hours. The reaction solution was heated to dissolve precipitated product and was filtered hot to remove the catalyst. The filtrate was concentrated and, after addition of toluene, again concentrated. 100 mg (100%) of the desired product were obtained.

i) 1-(2-Chloro-4,5-difluorobenzoyl)-3-(6-methoxy-2,4-dioxo-1,2,3,4-tetrahydro-quinazolin-7-yl)urea 100 mg (0.53 mmol) of 7-amino-6-methoxy-1H-quinazoline-2,4-dione were suspended in 20 ml of acetonitrile and 2 ml of N-methyl-2-pyrrolidinone, and 200 mg (0.97 mmol) of 2-chloro-4,5-difluorobenzoyl isocyanate (example 1a) were added. The reaction mixture was heated to boiling and then quenched with methanol and concentrated in vacuo. The residue was stirred with acetonitrile, and the resulting precipitate was filtered off. 64 mg (30%) of the desired product were obtained.

All documents referred to herein are incorporated herein by reference in their entirety, including the priority documents, DE 10231371.7-42 filed Jul. 11, 2002, and U.S. Provisional No. 60/425,600, filed Nov. 12, 2002.

What is claimed is:

1. A pharmaceutical composition comprising one or more active compounds and at least one other active ingredient in a pharmaceutically acceptable carrier, wherein said one or more active compounds are according to Formula I:

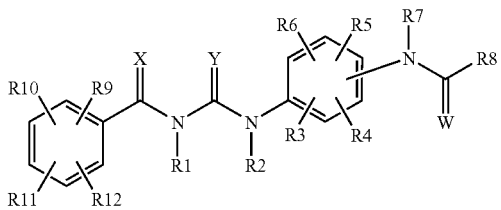

in which

W, X, Y are, independently of one another, O or S;

R9, R10, R11, R12 are, independently of one another, H, F, Cl, Br, OH, $CF_3$, $NO_2$, CN, $OCF_3$, O—($C_1$-$C_6$)-alkyl, O—($C_2$-$C_6$)-alkenyl, O—($C_2$-$C_6$)-alkynyl, O—$SO_2$—($C_1$-$C_4$)-alkyl, O—$SO_2$-phenyl, where the phenyl ring may be substituted up to twice by F, Cl, Br, CN, OR13, R13, $CF_3$, $OCF_3$, COOR13 or CON(R14)(R15), S—($C_1$-$C_6$)-alkyl, S—($C_2$-$C_6$)-alkenyl, S—($C_2$-$C_6$)-alkynyl, SO—($C_1$-$C_6$)-alkyl, $SO_2$—($C_1$-$C_6$)-alkyl, $SO_2$—$NH_2$, ($C_1$-$C_6$)-alkyl, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkyl, ($C_0$-$C_6$)-alkylene-COOR13, CON(R14)(R15), ($C_0$-$C_6$)-alkylene-N(R14)(R15), NH—COR13, NH—CO-phenyl, or NH—$SO_2$-phenyl or phenyl, where the phenyl ring may be substituted up to twice by F, Cl, Br, CN, OR13, R13, $CF_3$, $OCF_3$, COOR13 or CON(R14)(R15);

R13 is H, ($C_1$-$C_6$)-alkyl, ($C_2$-$C_6$)-alkenyl, ($C_2$-$C_6$)-alkynyl, ($C_3$-$C_7$)-cycloalkyl or ($C_3$-$C_7$)-cycloalkyl-($C_1$-$C_4$)-alkyl;

R1, R2 are, independently of one another, H, ($C_1$-$C_6$)-alkyl, where alkyl may be substituted by OH, O—($C_1$-$C_4$)-alkyl or N(R14)(R15), or O—($C_1$-$C_6$)-alkyl, O—($C_2$-$C_6$)-alkenyl, O—($C_2$-$C_6$)-alkynyl, CO—($C_1$-$C_6$)-alkyl, CO—($C_2$-$C_6$)-alkenyl, CO—($C_2$-$C_6$)-alkynyl, or COOR13 or ($C_0$-$C_6$)-alkylene-COOR13;

R3, R4, R5, R6 are, independently of one another, H, F, Cl, Br, OH, $CF_3$, $NO_2$, CN, $OCF_3$, ($C_1$-$C_6$)-alkyl, ($C_2$-$C_6$)-alkenyl, ($C_2$-$C_6$)-alkynyl, O—($C_1$-$C_{10}$)-alkyl, O—($C_2$-$C_{10}$)-alkenyl, O—($C_2$-$C_{10}$)-alkynyl, S—($C_1$-$C_6$)-alkyl, S—($C_2$-$C_6$)-alkenyl, S—($C_2$-$C_6$)-alkynyl, ($C_3$-$C_7$)-cycloalkyl, ($C_3$-$C_7$)-cycloalkyl-($C_1$-$C_4$)-alkyl, where alkyl, alkenyl, alkynyl and cycloalkyl may be substituted more than once by F, Cl, Br, SO-phenyl, $SO_2$-phenyl, where the phenyl ring may be substituted by F, Cl, Br or R13, or OR13, COOR13, CON(R14)(R15), N(R14)(R15) or CO-heteroalkyl, O—SO—($C_1$-$C_6$)-alkyl, O—$SO_2$—($C_1$-$C_6$)-alkyl, O—$SO_2$—($C_6$-$C_{10}$)-aryl, O—($C_6$-$C_{10}$)-aryl, where aryl may be substituted up to twice by F, Cl, CN, OR13, R13, $CF_3$ or $OCF_3$, SO—($C_1$-$C_6$)-alkyl, $SO_2$—($C_1$-$C_6$)-alkyl, $SO_2$—($C_6$-$C_{10}$)-aryl, where the phenyl ring may be substituted up to twice by F, Cl, Br, CN, OR13, R13, $CF_3$, $OCF_3$, COOR13 or CON(R14)(R15), $SO_2$—N(R14)(R15), COOR13, CO-heteroalkyl, N(R14)(R15) or heteroalkyl;

R14, R15 are, independently of one another, H, ($C_1$-$C_6$)-alkyl, where alkyl may be substituted by N(R13)$_2$, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkyl, CO—($C_1$-$C_6$)-alkyl, COO—($C_1$-$C_6$)-alkyl, COO—($C_1$-$C_6$)-alkylene-OCO—($C_1$-$C_6$)-alkyl, CO-phenyl, COO-phenyl, COO—($C_1$-$C_6$)-alkenyl-phenyl, OH, O—($C_1$-$C_6$)-alkyl, O—($C_1$-$C_6$)-alkenyl-phenyl or $NH_2$;

or the radicals R14 and R15 form with the nitrogen atom to which they are bonded a 3-7-membered, saturated heterocyclic ring which may comprise up to 3 heteroatoms selected from N, O or S, where the heterocyclic ring may be substituted up to three times by F, Cl, Br, OH, oxo, N(R16)(R17) or ($C_1$-$C_4$)-alkyl;

R16, R17 are, independently of one another, H, ($C_1$-$C_6$)-alkyl, where alkyl may be substituted by N(R13)$_2$, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkyl, CO—($C_1$-$C_6$)-alkyl, COO—($C_1$-$C_6$)-alkyl, COO—($C_1$-$C_6$)-alkylene-OCO—($C_1$-$C_6$)-alkyl, CO-phenyl, COO-phenyl, COO—($C_1$-$C_6$)-alkenyl-phenyl, OH, O—($C_1$-$C_6$)-alkyl, O—($C_1$-$C_6$)-alkenyl-phenyl or $NH_2$;

heteroalkyl is a 3-7-membered, saturated or up to triunsaturated heterocyclic ring which may comprise up to 4 heteroatoms selected from N, O or S, where the heterocyclic ring may be substituted up to three times by F, Cl, Br, CN, oxo, ($C_1$-$C_4$)-alkyl, ($C_0$-$C_4$)-alkylene-COOR13, CON(R14)(R15), OR13, N(R14)(R15) or phenyl, where phenyl may be substituted by COOR13;

R7 is H, ($C_1$-$C_6$)-alkyl, where alkyl may be substituted by OR13 or N(R14)(R15), O—($C_1$-$C_6$)-alkyl, CO—($C_1$-$C_6$)-alkyl, ($C_1$-$C_6$)-alkylene-COOR13, or COOR13;

R8 is OR20; or R8 and R4 together form the group —NH—CO—;

R18, R19 are, independently of one another, H, ($C_1$-$C_{10}$)-alkyl, ($C_2$-$C_{10}$)-alkenyl, ($C_2$-$C_{10}$)-alkynyl, ($C_3$-$C_7$)-cycloalkyl, ($C_3$-$C_7$)-cycloalkyl-($C_1$-$C_6$)-alkyl, ($C_6$-$C_{10}$)-aryl, ($C_6$-$C_{10}$)-aryl-($C_1$-$C_4$)-alkyl, ($C_6$-$C_{10}$)-aryl-($C_2$-$C_4$)-alkenyl, ($C_6$-$C_{10}$)-aryl-($C_2$-$C_4$)-alkynyl, heteroaryl, heteroaryl-($C_1$-$C_4$)-alkyl, heteroaryl-($C_2$-$C_4$)-alkenyl, heteroaryl-($C_2$-$C_4$)-alkynyl, where alkyl, alkenyl, alkynyl and cycloalkyl may be substituted one or more times by F, Cl, CN, OR13, R13, $CF_3$, $OCF_3$, ($C_6$-$C_{10}$)-aryl, NH—C(=NR14)—N(R14)(R15), N(R14)(R15), C(=NR14)—N(R14)(R15), COOR13 or CON(R14)(R15), and where aryl may be substituted more than once by F, Cl, CN, O—($C_1$-$C_6$)-alkyl, O—($C_2$-$C_6$)-alkenyl, ($C_1$-$C_6$)-alkyl, ($C_2$-$C_6$)-alkenyl, CO—($C_1$-$C_6$)-alkyl, CO—($C_2$-$C_6$)-alkenyl, where alkyl and alkenyl may be substituted more than once by F, Cl, $CH_3$, $OCH_3$ or CN, NH—C(=NR14)—N(R14)(R15), N(R14)(R15), C(=NR14)—N(R14)(R15), COOR13, CON(R14)(R15), O-phenyl, phenyl or pyridyl; COOR13, CON—(R14)(R15), CO-heteroalkyl, CO—($C_6$-$C_{10}$)-aryl or $SO_2$—($C_6$-$C_{10}$)-aryl, where aryl may be substituted up to twice by F, Cl, CN, OH, ($C_1$-$C_6$)-alkyl, O—($C_1$-$C_6$)-alkyl, $CF_3$, $OCF_3$, COOR13 or CON(R14)(R15);

or the radicals R18 and R19 form with the nitrogen atom to which they are bonded a 3-7-membered, saturated heterocyclic ring which may comprise up to 3 heteroatoms selected from the group of N, O or S, where the heterocyclic ring may be substituted up to three times by F, Cl, Br, OH, oxo, N(R16)(R17) or ($C_1$-$C_4$)-alkyl;

R20 is ($C_1$-$C_{10}$)-alkyl, ($C_2$-$C_{10}$)-alkenyl, ($C_2$-$C_{10}$)-alkynyl, ($C_3$-$C_7$)-cycloalkyl, ($C_3$-$C_7$)-cycloalkyl-($C_1$-$C_6$)-alkyl, ($C_6$-$C_{10}$)-aryl, ($C_6$-$C_{10}$)-aryl-($C_1$-$C_4$)-alkyl, ($C_6$-$C_{10}$)-aryl-($C_2$-$C_4$)-alkenyl or ($C_6$-$C_{10}$)-aryl-($C_2$-$C_4$)-alkynyl, where aryl may be substituted more than once by F, Cl, CN, O—($C_1$-$C_6$)-alkyl, O—($C_2$-$C_6$)-alkenyl, ($C_1$-$C_6$)-alkyl, ($C_2$-$C_6$)-alkenyl, CO—($C_1$-$C_6$)-alkyl, CO—($C_2$-$C_6$)-alkenyl, where alkyl and alkenyl may be substituted more than once by F, Cl, $CH_3$, $OCH_3$ or CN, NH—C(=NR14)—N(R14)(R15), N(R14)(R15), C(=NR14)—N(R14)(R15), COOR13, CON(R14)(R15), O-phenyl, phenyl or pyridyl, where phenyl may be substituted by F, Cl, CN or ($C_1$-$C_6$)-alkyl;

and physiologically tolerated salts of Formula I;

and wherein the at least one other active ingredient is selected from antidiabetics, hypoglycemic active ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists (bromocriptine, Doprexin), lipase/amylase inhibitors, PPAR modulators, RXR modulators, and TR-β agonists or amphetamines.

2. A process for producing a pharmaceutical composition of claim 1, the process comprising mixing one or more of the active compounds of Formula I of claim 1 with at least one other active ingredient of claim 1 and a pharmaceutically suitable carrier, and converting this mixture into a form suitable for administration.

3. A pharmaceutical composition comprising one or more active compounds in a pharmaceutically acceptable carrier, wherein said active compounds are according to Formula Ia:

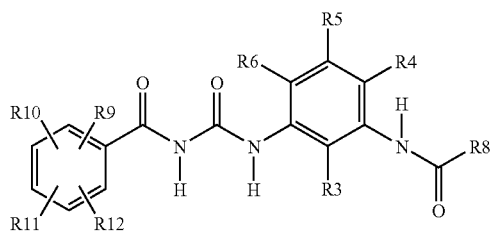

Ia wherein
R9, R10, R11 are independently selected from F and Cl;
R12 is H;
R13 is H, $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkyl;
R3, R4, R5, and R6 are independently of one another H, F, Cl, Br, OH, $CF_3$, $NO_2$, CN, $OCF_3$, $(C_1-C_6)$-alkyl, $(C_2-C_6)$-alkenyl, $(C_2-C_6)$-alkynyl, O—$(C_1-C_{10})$-alkyl, O—$(C_2-C_{10})$-alkenyl, O—$(C_2-C_{10})$-alkynyl, S—$(C_1-C_6)$-alkyl, S—$(C_2-C_6)$-alkenyl, S—$(C_2-C_6)$-alkynyl, $(C_3-C_7)$-cycloalkyl, $(C_3-C_7)$-cycloalkyl-$(C_1-C_4)$-alkyl, where alkyl, alkenyl, alkynyl and cycloalkyl may be substituted more than once by F, Cl, Br, SO-phenyl, $SO_2$-phenyl, where the phenyl ring may be substituted by F, Cl, Br or R13, or OR13, COOR13, CON(R14)(R15), N(R14)(R15) or CO-heteroalkyl, O—SO—$(C_1-C_6)$-alkyl, O—$SO_2$—$(C_1-C_6)$-alkyl, O—$SO_2$—$(C_6-C_{10})$-aryl, O—$(C_6-C_{10})$-aryl, where aryl may be substituted up to twice by F, Cl, CN, OR13, R13, $CF_3$ or $OCF_3$, SO—$(C_1-C_6)$-alkyl, $SO_2$—$(C_1-C_6)$-alkyl, $SO_2$—$(C_6-C_{10})$-aryl, where the phenyl ring may be substituted up to twice by F, Cl, Br, CN, OR13, R13, $CF_3$, $OCF_3$, COOR13 or CON(R14)(R15), $SO_2$—N(R14)(R15), COOR13, CO-heteroalkyl, N(R14)(R15) or heteroalkyl;
R14, R15 are independently selected from H and $(C_1-C_6)$-alkyl, wherein alkyl may be substituted by $N(R13)_2$;
R16, R17 independently of one another are H, $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkyl, CO—$(C_1-C_6)$-alkyl, COO—$(C_1-C_6)$-alkyl, COO—$(C_1-C_6)$-alkylene-OCO—$(C_1-C_6)$-alkyl, CO-phenyl, COO-phenyl, COO—$(C_1-C_6)$-alkenyl-phenyl, OH, O—$(C_1-C_6)$-alkyl, O—$(C_1-C_6)$-alkenyl-phenyl or $NH_2$, wherein said $(C_1-C_6)$-alkyl may be substituted by $N(R13)_2$;
heteroalkyl is a 3-7-membered, saturated or up to triunsaturated heterocyclic ring which may comprise up to 4 heteroatoms selected from N, O, and S, wherein the heterocyclic ring may be substituted up to three times by F, Cl, Br, CN, oxo, $(C_1-C_4)$-alkyl, COOR13, $(C_1-C_4)$-alkylene-COOR13, CON(R14)(R15), OR13, N(R14)(R15), or phenyl, wherein phenyl may be substituted by COOR13;
R8 is OR20;
or R8 and R4 together form the group —NH—CO—;
R18, R19 independently of one another are selected from H, $(C_1-C_{10})$-alkyl, $(C_2-C_{10})$-alkenyl, $(C_2-C_{10})$-alkynyl, $(C_3-C_7)$-cycloalkyl, $(C_3-C_7)$-cycloalkyl-$(C_1-C_6)$-alkyl, $(C_6-C_{10})$-aryl, $(C_6-C_{10})$-aryl-$(C_1-C_4)$-alkyl, $(C_6-C_{10})$-aryl-$(C_2-C_4)$-alkenyl, $(C_6-C_{10})$-aryl-$(C_2-C_4)$-alkynyl, heteroaryl, heteroaryl-$(C_1-C_4)$-alkyl, heteroaryl-$(C_2-C_4)$-alkenyl, and heteroaryl-$(C_2-C_4)$-alkynyl, where alkyl, alkenyl, alkynyl and cycloalkyl may be substituted more than once by F, Cl, CN, OR13, R13, $CF_3$, $OCF_3$, $(C_6-C_{10})$-aryl, NH—C(=NR14)—N(R14)(R15), N(R14)(R15), C(=NR14)—N(R14)(R15), COOR13 or CON(R14)(R15), and where aryl may be substituted more than once by F, Cl, CN, O—$(C_1-C_6)$-alkyl, O—$(C_2-C_6)$-alkenyl, $(C_1-C_6)$-alkyl, $(C_2-C_6)$-alkenyl, CO—$(C_1-C_6)$-alkyl, CO—$(C_2-C_6)$-alkenyl, where alkyl and alkenyl may be substituted more than once by F, Cl, $CH_3$, $OCH_3$, CN, NH—C(=NR14)—N(R14)(R15), N(R14)(R15), C(=NR14)—N(R14)(R15), COOR13, CON(R14)(R15), O-phenyl, phenyl, pyridyl, COOR13, CON—(R14)(R15), CO-heteroalkyl, CO—$(C_6-C_{10})$-aryl or $SO_2$—$(C_6-C_{10})$-aryl, where aryl may be substituted up to twice by F, Cl, CN, OH, $(C_1-C_6)$-alkyl, O—$(C_1-C_6)$-alkyl, $CF_3$, $OCF_3$, COOR13 or CON(R14)(R15);
or the radicals R18 and R19 form together with the nitrogen atom to which they are bonded a 3-7-membered, saturated heterocyclic ring which may comprise up to two further heteroatoms selected from the group of N, O, and S, where the heterocyclic ring may be substituted up to three times by F, Cl, Br, OH, oxo, N(R16)(R17), or $(C_1-C_4)$-alkyl;
R20 is $(C_1-C_{10})$-alkyl, $(C_2-C_{10})$-alkenyl, $(C_2-C_{10})$-alkynyl, $(C_3-C_7)$-cycloalkyl, $(C_3-C_7)$-cycloalkyl-$(C_1-C_6)$-alkyl, $(C_6-C_{10})$-aryl, $(C_6-C_{10})$-aryl-$(C_1-C_4)$-alkyl, $(C_6-C_{10})$-aryl-$(C_2-C_4)$-alkenyl or $(C_6-C_{10})$-aryl-$(C_2-C_4)$-alkynyl, where aryl may be substituted more than once by F, Cl, CN, O—$(C_1-C_6)$-alkyl;
and physiologically tolerated salts of Formula Ia.

* * * * *